US009725476B2

(12) United States Patent
Beers et al.

(10) Patent No.: US 9,725,476 B2
(45) Date of Patent: Aug. 8, 2017

(54) SILYLATED METAL COMPLEXES

(75) Inventors: Scott Beers, Flemington, NJ (US); Chuanjun Xia, Lawrenceville, NJ (US); Suman Layek, Lawrenceville, NJ (US); Harvey Wendt, Medford Lakes, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 804 days.

(21) Appl. No.: 13/544,622

(22) Filed: Jul. 9, 2012

(65) Prior Publication Data

US 2014/0008617 A1    Jan. 9, 2014

(51) Int. Cl.
*H01L 51/50* (2006.01)
*C07F 15/00* (2006.01)
*H01L 51/00* (2006.01)

(52) U.S. Cl.
CPC ...... *C07F 15/0033* (2013.01); *H01L 51/0085* (2013.01); *H01L 51/0094* (2013.01); *H01L 51/006* (2013.01); *H01L 51/0074* (2013.01); *H01L 51/5012* (2013.01)

(58) Field of Classification Search
CPC ............. H01L 51/0094; H01L 51/0085; H01L 51/5012; H01L 51/5016; H01L 51/0074; H01L 51/006; C07F 15/0033; C09K 11/06; C09K 2211/1029; C09K 2211/185
USPC ......... 428/690, 917; 313/504, 506; 548/103, 548/108; 546/4, 10
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 2001/0019782 A1* | 9/2001 | Igarashi | C07F 15/0033 428/690 |
| 2002/0024293 A1* | 2/2002 | Igarashi et al. | 313/483 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0151042 A1 | 8/2003 | Hueschen | |
| 2003/0152802 A1 | 8/2003 | Tsuboyama et al. | |
| 2003/0175553 A1 | 9/2003 | Thompson et al. | |
| 2003/0230980 A1 | 12/2003 | Forrest et al. | |
| 2004/0013905 A1* | 1/2004 | Tsuboyama et al. | 428/690 |
| 2004/0036077 A1 | 2/2004 | Ise | |
| 2004/0137267 A1* | 7/2004 | Igarashi | C09K 11/06 428/690 |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Zhou et al., Robust Tris-Cyclometalated Iridium(III) Phosphors with Ligands for Effective Charge Carrer Injection/Transport: Synthesis, Redox, Photophysical, and Electrophosphorescent Behavior. Chemistry an Asian Journal. 2008, 3, 1830-1841.*
Jung et al., A green emitting iridium(III) complex with narrow emission band and its application to phosphorescence organic light-emitting diodes (OLEDs). Organic Electronics. 10 (2009) 1066-1073.*
Jung and Kim et al., "Effective Electrophosphorescence Emitting Devices by Using New Type Ir(III) Complex with Bluky Substituent Spacers" (sic), 2006, vol. 444, pp. 95-101.*
Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Jennifer Chriss
*Assistant Examiner* — Dylan Kershner
(74) *Attorney, Agent, or Firm* — Duane Morris LLP

(57) ABSTRACT

Novel metal complexes containing silyl substitution are provided. Depending on the location of the substitution, compounds that emit in the yellow or green portions of the spectrum can be produced. These compounds are useful as components of OLED devices.

13 Claims, 3 Drawing Sheets

(56) References Cited

U.S. PATENT DOCUMENTS

| | | |
|---|---|---|
| 2005/0260449 A1 | 11/2005 | Walters et al. |
| 2006/0008670 A1 | 1/2006 | Lin et al. |
| 2006/0008673 A1* | 1/2006 | Kwong .............. C07F 15/0033 428/690 |
| 2006/0202190 A1* | 9/2006 | Funahashi ................ 257/40 |
| 2006/0202194 A1 | 9/2006 | Jeong et al. |
| 2006/0228582 A1* | 10/2006 | Ragini .............. C07F 15/0033 428/690 |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0247061 A1* | 10/2007 | Adamovich et al. ......... 313/504 |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0074033 A1* | 3/2008 | Ionkin et al. ................. 313/504 |
| 2008/0106190 A1 | 5/2008 | Yabunouchi et al. |
| 2008/0124572 A1 | 5/2008 | Mizuki et al. |
| 2008/0220265 A1* | 9/2008 | Xia .................... H01L 51/0025 428/447 |
| 2008/0233433 A1* | 9/2008 | Igarashi et al. ............... 428/704 |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1* | 4/2009 | Kwong .............. H01L 51/0085 313/504 |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2009/0189520 A1* | 7/2009 | Kim et al. .................... 313/504 |
| 2010/0270916 A1* | 10/2010 | Xia et al. ...................... 313/504 |
| 2011/0049496 A1* | 3/2011 | Fukuzaki ............ C07F 15/0033 257/40 |
| 2011/0227049 A1* | 9/2011 | Xia .................... C07F 15/0033 257/40 |

FOREIGN PATENT DOCUMENTS

| | | |
|---|---|---|
| EP | 2034538 | 3/2009 |
| JP | 2005011610 | 1/2005 |
| JP | 2005327526 | 11/2005 |
| JP | 2006019543 | 1/2006 |
| JP | 2007123392 | 5/2007 |
| JP | 2007254297 | 10/2007 |
| JP | 2008074939 | 4/2008 |
| JP | 2009191066 | 8/2009 |
| KR | 20110111691 | 10/2011 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006067074 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | WO 2009021126 A2 * | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato)beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

(56) References Cited

OTHER PUBLICATIONS

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).
Lo, Shih-Chun et al., "Blue Phosphorescence from Indium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N-Co-ordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

SILYLATED METAL COMPLEXES

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel metal complexes containing a silyl group substitution that are suitable for use in OLED devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

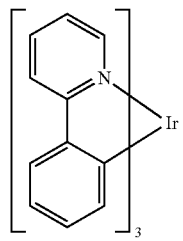

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound comprising the formula $M(L_1)_m(L_2)_n$ is provided. Ligand $L_1$ is a first ligand having the formula:

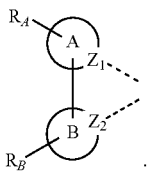

Formula I

Ligand $L_2$ is a second ligand having the formula:

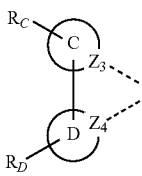

Formula II $L_1$ is different from $L_2$. A, B, C, and D are each independently a 5 or 6-membered carbocyclic or heterocyclic ring, and $Z_1$, $Z_2$, $Z_3$, and $Z_4$ are each independently selected from the group consisting of C or N. $R_A$, $R_B$, $R_C$ and $R_D$ each represent mono, di, tri, or tetra substitutions or no substitution, and any two adjacent substituents are optionally joined together to form a ring, which may be further substituted. At least one of $R_A$, $R_B$, $R_C$, and $R_D$ is $SiR_1R_2R_3$, wherein at least one of $R_1$, $R_2$, and $R_3$ is aryl or heteroaryl, which may be further substituted.

Each of $R_A$, $R_B$, $R_Q$, $R_D$, $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfonyl, sulfinyl, sulfonyl, phosphine, and combinations thereof.

M is a metal, m is an integer of at least 1, n is an integer of at least 1, and m+n is the maximum number of ligands that may be attached to metal M. Each $L_1$ and $L_2$ may be optionally linked with each other to comprise a tetradentate, or hexadentate ligand.

In one aspect, $L_1$ has the formula:

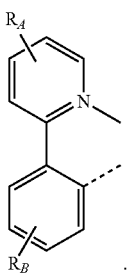

Formula III

In one aspect, $L_2$ has the formula:

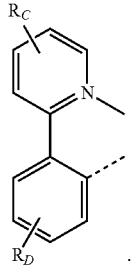

Formula IV

In one aspect, M is Ir.

In one aspect, the compound has the formula:

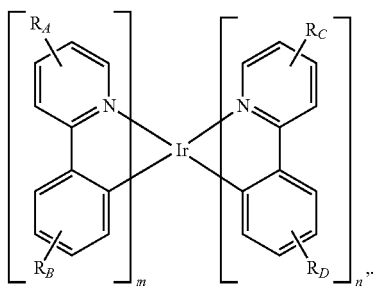

Formula V

In one aspect, m=1 and n=2, and at least one of $R_A$ or $R_B$ comprises $SiR_1R_2R_3$, and wherein none of $R_C$ or $R_D$ contain silicon.

In one aspect, at least one of $R_A$, $R_B$, $R_C$, or $R_D$ is deuterated or partially deuterated.

In one aspect, $R_1$, $R_2$, and $R_3$ are aryl or heteroaryl, which may be further substituted.

In one aspect, $R_1$ is alkyl or cycloalkyl, $R_2$ and $R_3$ are aryl or heteroaryl, which may be further substituted.

In one aspect, $R_1$ and $R_2$ are alkyl or cycloalkyl, $R_3$ is aryl or heteroaryl, which may be further substituted.

In one aspect, $R_1$, $R_2$, and $R_3$ are each independently selected from the group consisting of: methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, and 2,6-diisopropylphenyl.

In one aspect, $R_1$, $R_2$, and $R_3$ are phenyl.

In one aspect, $R_1$ is methyl, and $R_2$ and $R_3$ are phenyl.

In one aspect, $R_1$ and $R_2$ are methyl, $R_3$ is phenyl.

In one aspect, the compound is selected from the group consisting of Compound 1-Compound 36.

In one aspect, a first device is provided. The first device comprises a first organic light emitting device, further comprising: an anode, a cathode, and an organic layer, disposed between the anode and the cathode, comprising a compound having the formula $M(L_1)_m(L_2)_n$. Ligand $L_1$ is a first ligand having the formula:

Formula I

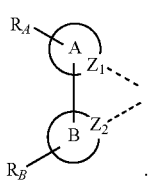

Ligand $L_2$ is a second ligand having the formula:

Formula II

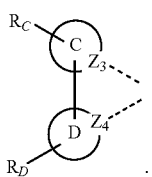

$L_1$ is different from $L_2$. A, B, C, and D are each independently a 5 or 6-membered carbocyclic or heterocyclic ring, and $Z_1$, $Z_2$, $Z_3$, and $Z_4$ are each independently selected from the group consisting of C or N. $R_A$, $R_B$, $R_C$ and $R_D$ each represent mono, di, tri, or tetra substitutions or no substitution, and any two adjacent substituents are optionally joined together to form a ring, which may be further substituted. At least one of $R_A$, $R_a$, $R_C$, and $R_D$ is $SiR_1R_2R_3$, wherein at least one of $R_1$, $R_2$, and $R_3$ is aryl or heteroaryl, which may be further substituted;

Each of $R_A$, $R_B$, $R_C$, $R_D$, $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

M is a metal, m is an integer of at least 1, n is an integer of at least 1, and m+n is the maximum number of ligands that may be attached to metal M. Each $L_1$ and $L_2$ may be optionally linked with each other to comprise a tetradentate, or hexadentate ligand.

In one aspect, the first device is a consumer product.

In one aspect, the first device is an organic light-emitting device.

In one aspect, the first device comprises a lighting panel.

In one aspect, the organic layer is an emissive layer and the compound is an emissive dopant.

In one aspect, the organic layer is an emissive layer and the compound is a non-emissive dopant.

In one aspect, the organic layer further comprises a host.

In one aspect, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡CH$C_nH_{2n+1}$, $Ar_1$, $Ar_1$—$Ar_2$, $C_nH_{2n}$—$Ar_1$, or no substitution, wherein n is from 1 to 10; and wherein $Ar_1$ and $Ar_e$, are independently selected from the group consisting of benzene, biphenyl, naphthalene, triphenylene, carbazole, and heteroaromatic analogs thereof.

In one aspect, the host is selected from the group consisting of:

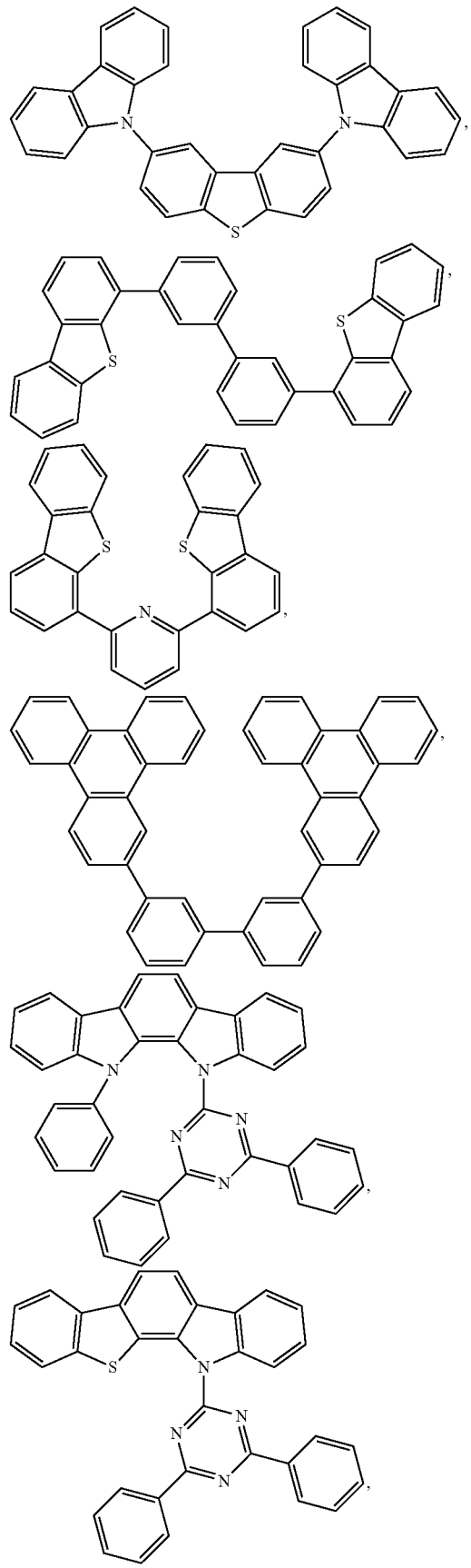

-continued

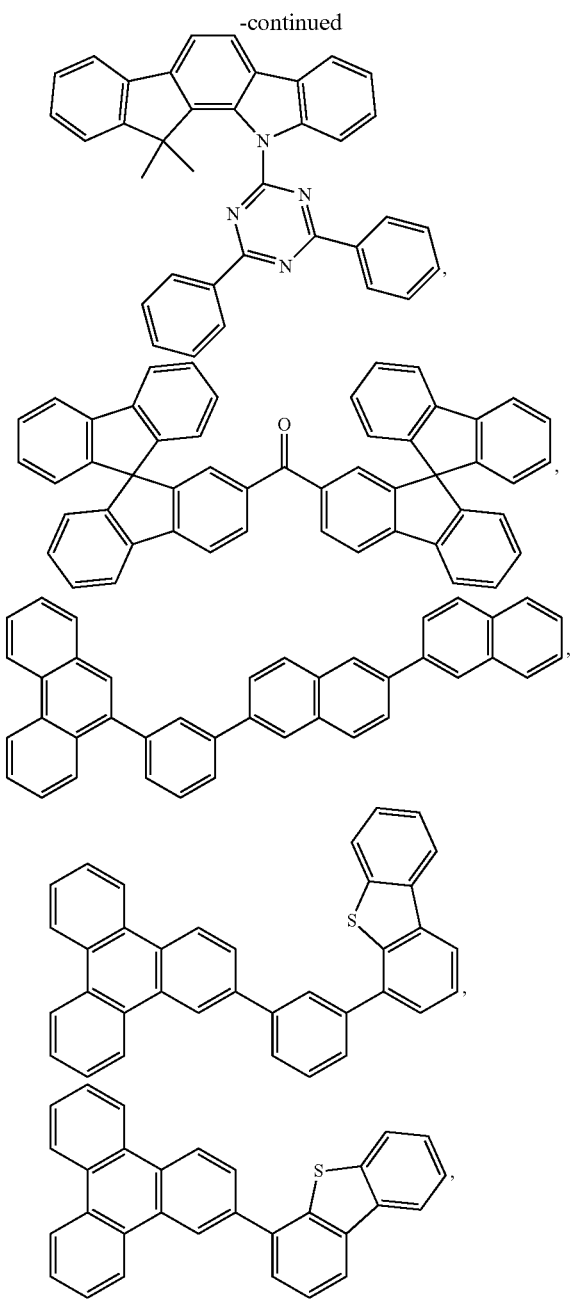

and combinations thereof.

In one aspect, the host comprises a metal complex.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
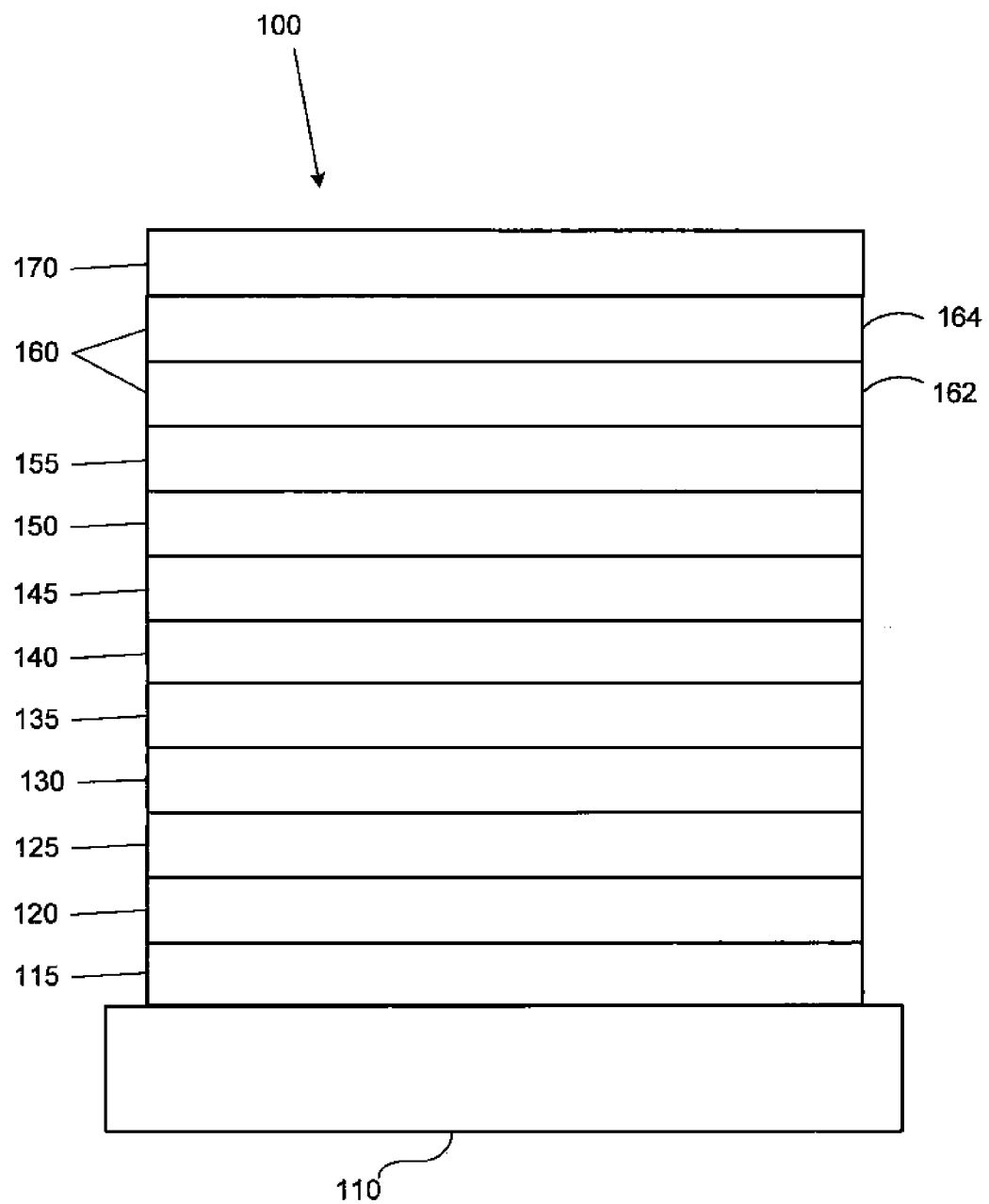
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
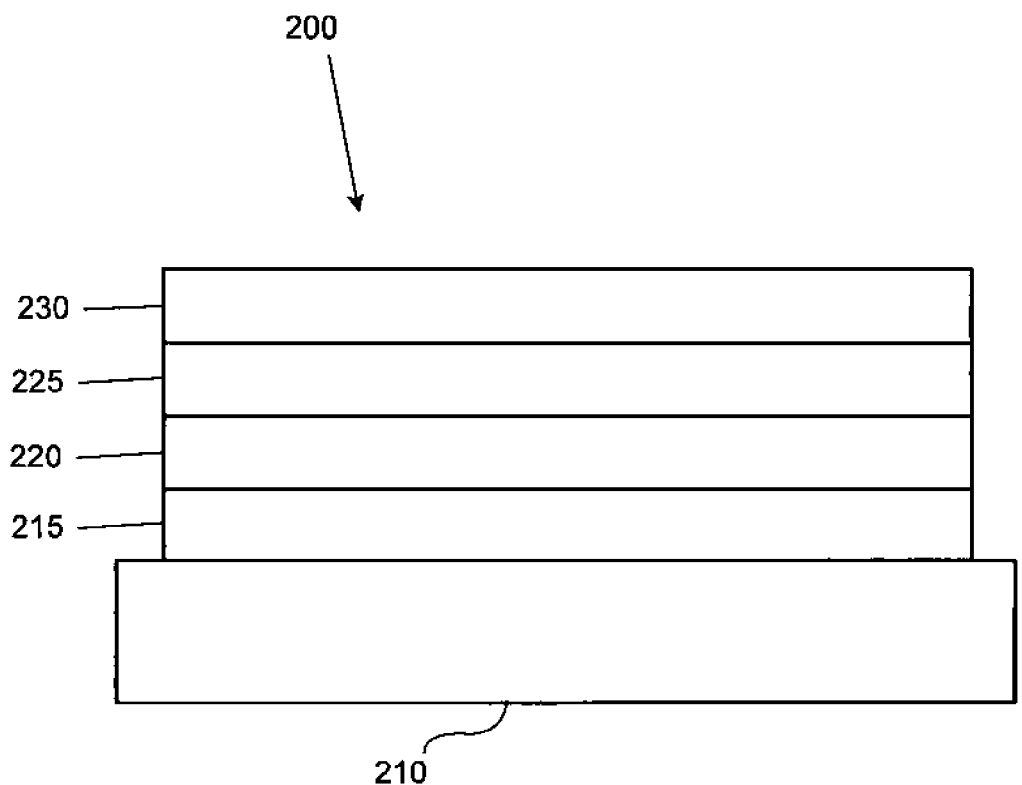
FIG. 2 shows an inverted organic light emitting device that does not have a separate electron transport layer.
Figure 3:
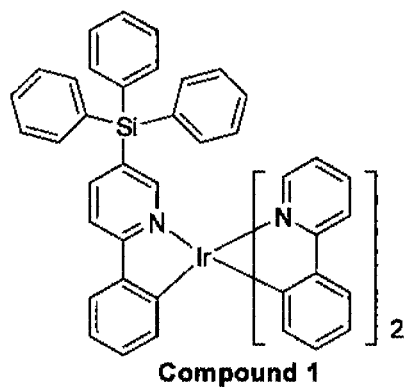
FIG. 3 shows an exemplary compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247, 190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A compound comprising the formula $M(L_1)_m(L_2)_n$ is provided. Ligand $L_1$ is a first ligand having the formula:

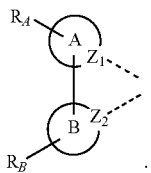

Formula I

Ligand $L_2$ is a second ligand having the formula:

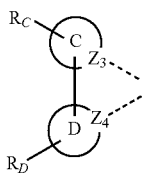

Formula II $L_1$ is different from $L_2$. A, B, C, and D are each independently a 5 or 6-membered carbocyclic or heterocyclic ring, and $Z_1$, $Z_2$, $Z_3$, and $Z_4$ are each independently selected from the group consisting of C or N. $R_A$, $R_B$, $R_C$ and $R_D$ each represent mono, di, tri, or tetra substitutions or no substitution, and any two adjacent substituents are optionally joined together to form a ring, which may be further substituted. At least one of $R_A$, $R_B$, $R_C$, and $R_D$ is $SiR_1R_2R_3$, wherein at least one of $R_1$, $R_2$, and $R_3$ is aryl or heteroaryl, which may be further substituted.

Each of $R_A$, $R_B$, $R_C$, $R_D$, $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof.

M is a metal, m is an integer of at least 1, n is an integer of at least 1, and m+n is the maximum number of ligands that may be attached to metal M. Each $L_1$ and $L_2$ may be optionally linked with each other to comprise a tetradentate, or hexadentate ligand.

The silyl group in Formula I has at least one aryl substituent. The aryl substitution on the silyl group improves the quantum yield of the compound and operational lifetime of OLEDs when compounds of Formula I are used. The bulkiness of the aryl substation prevents stacking of the compound in the solid state, which reduces quenching.

As described below, the devices made with compounds of Formula I showed improved lifetime. Compounds A-D were used as comparative compounds. They all have triisopropylsilyl substituents at various positions. Triisopropylsilyl group has significantly higher chemical stability compared to the trimethylsilyl group, and it was chosen for at least this reason.

In one embodiment, $L_1$ has the formula:

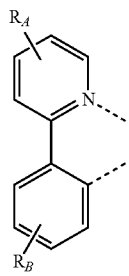

Formula III

In one embodiment, $L_2$ has the formula:

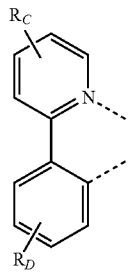

Formula IV

In one embodiment, M is Ir.
In one embodiment, the compound has the formula:

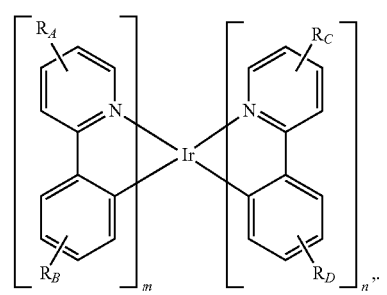

Formula V

In one embodiment, m=1 and n=2, and at least one of $R_A$ or $R_B$ comprises $SiR_1R_2R_3$, and wherein none of $R_C$ or $R_D$ contain silicon.

In one embodiment, at least one of $R_A$, $R_B$, $R_C$, or $R_D$ is deuterated or partially deuterated.

In one embodiment, $R_1$, $R_2$, and $R_3$ are aryl or heteroaryl, which may be further substituted.

In one embodiment, $R_1$ is alkyl or cycloalkyl, $R_2$ and $R_3$ are aryl or heteroaryl, which may be further substituted.

In one embodiment, $R_1$ and $R_2$ are alkyl or cycloalkyl, $R_3$ is aryl or heteroaryl, which may be further substituted.

In some embodiments, the silyl group contains both alkyl and aryl substitution. It is thought a silyl group that has mixed substitution allows for color tuning since replacement of an aryl group with an alkyl group may result in a blue shift. Additionally, aryl substitution is believed to provide good stability for the complex. Furthermore, mixing alkyl and aryl substitution on silicon may reduce the sublimation temperature of the compounds of Formula I, making them more suitable for manufacture of OLEDs by vacuum thermal evaporation.

In one embodiment, $R_1$, $R_2$, and $R_3$ are each independently selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, and 2,6-diisopropylphenyl.

In one embodiment, $R_1$, $R_2$, and $R_3$ are phenyl.

In one embodiment, $R_1$ is methyl, and $R_2$ and $R_3$ are phenyl.

In one embodiment, $R_1$ and $R_2$ are methyl, $R_3$ is phenyl.

In one embodiment, the compound is selected from the group consisting of:

Compound 1

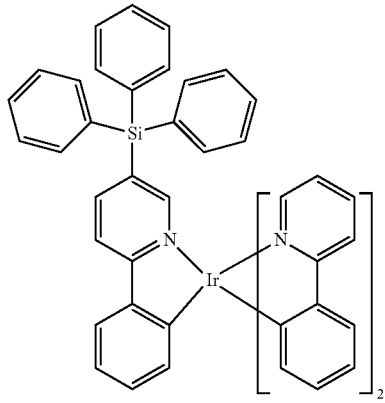

Compound 2

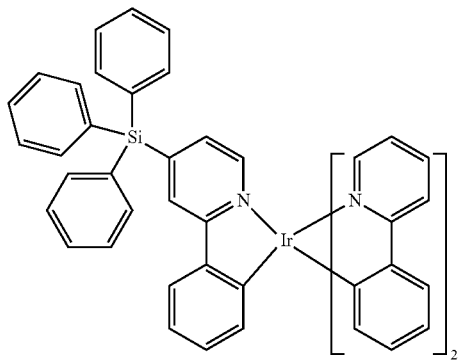

-continued

Compound 3

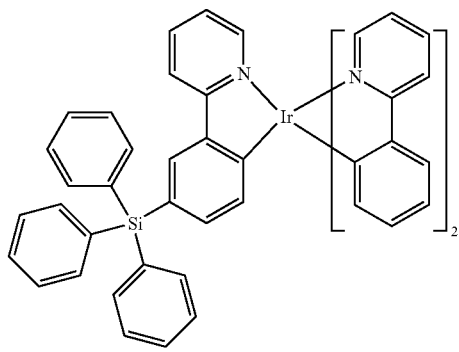

Compound 4

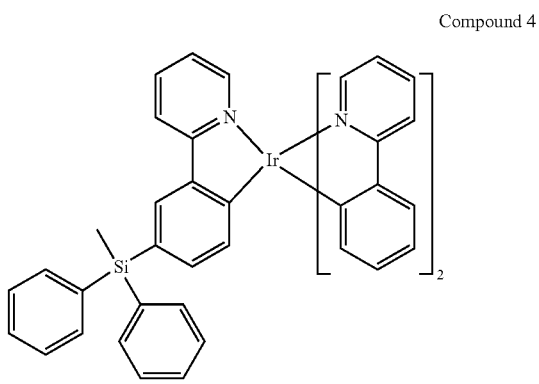

Compound 5

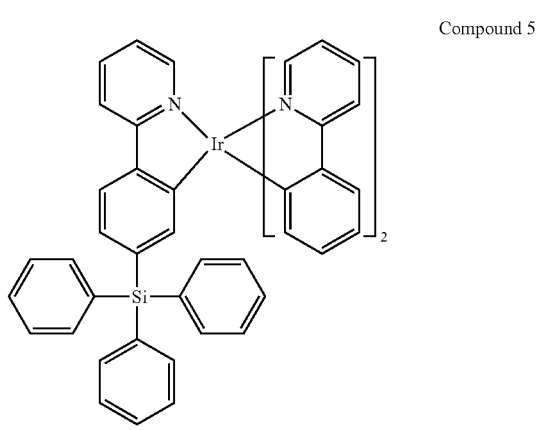

Compound 6

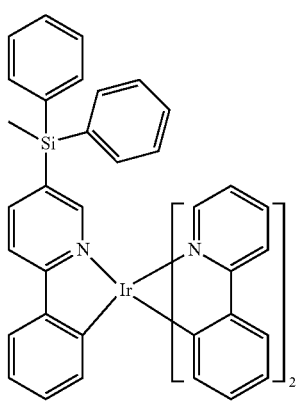

Compound 7
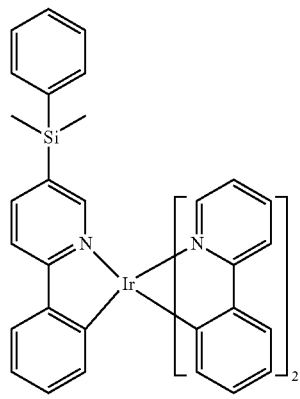
Compound 8
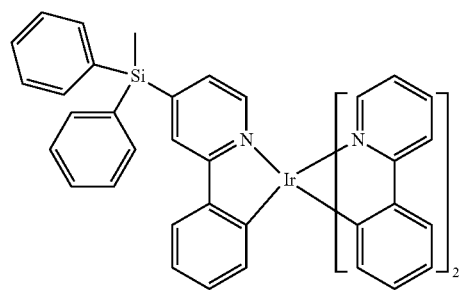
Compound 9
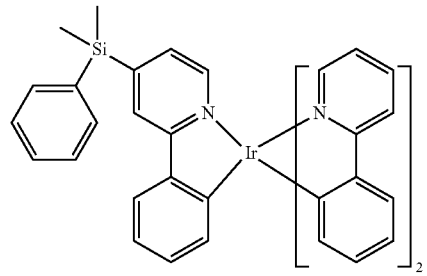
Compound 10
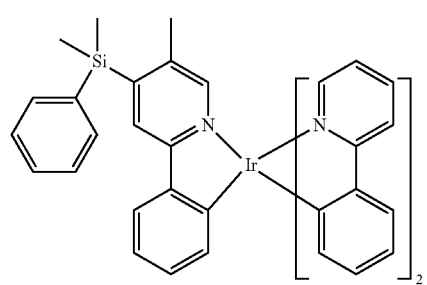
Compound 11
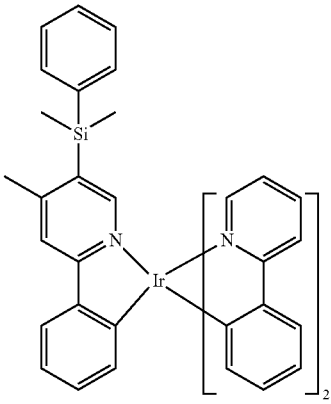
Compound 12
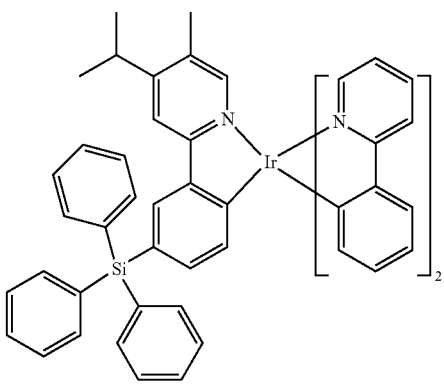
Compound 13
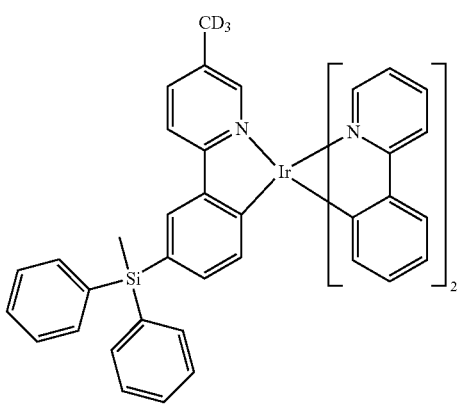
Compound 14
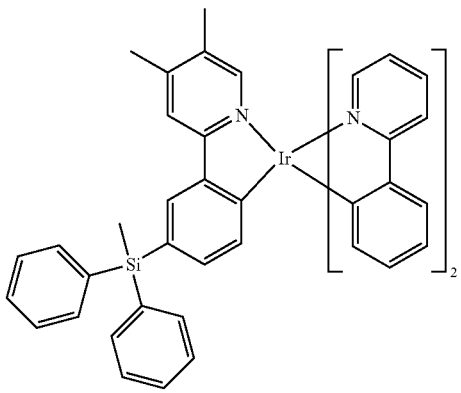

Compound 15
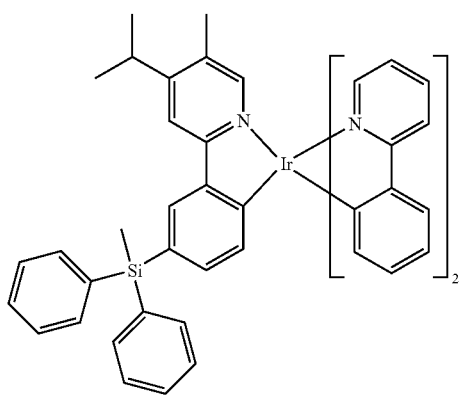
Compound 16
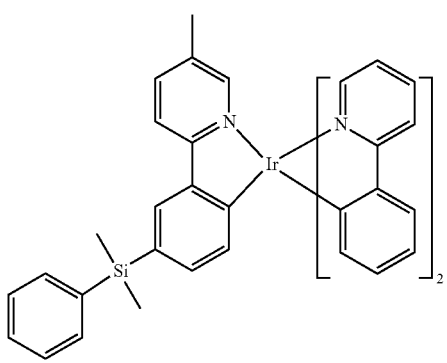
Compound 17
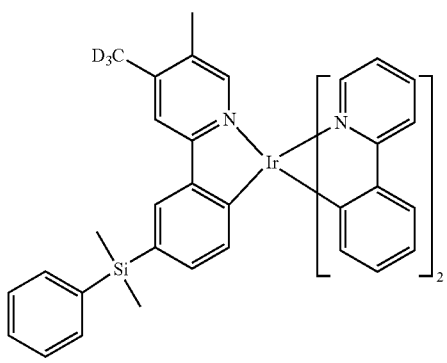
Compound 18
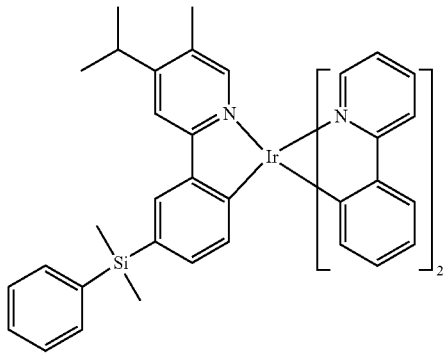
Compound 19
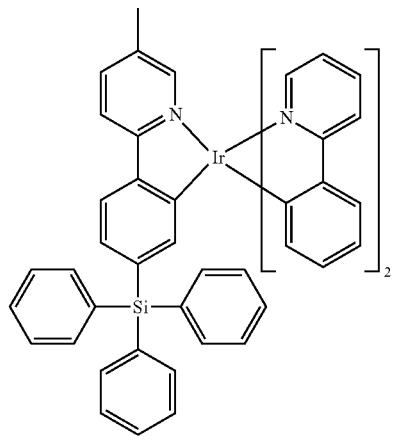
Compound 20
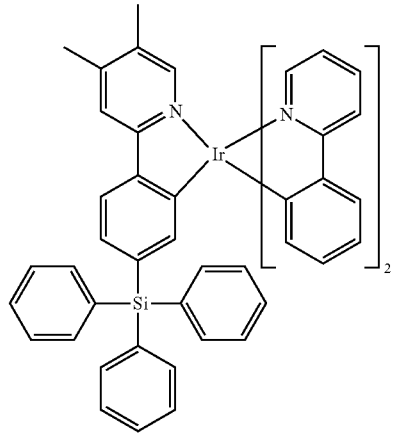
Compound 21
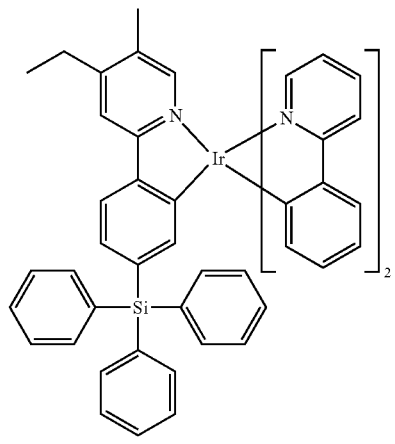

Compound 22
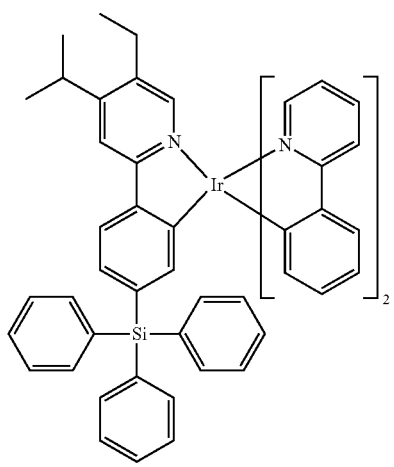
Compound 24
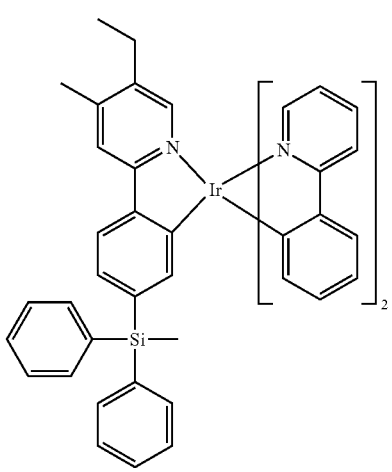
Compound 22
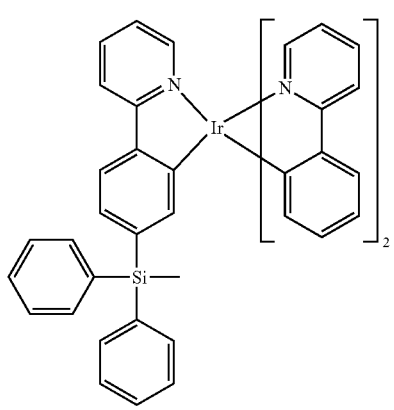
Compound 25
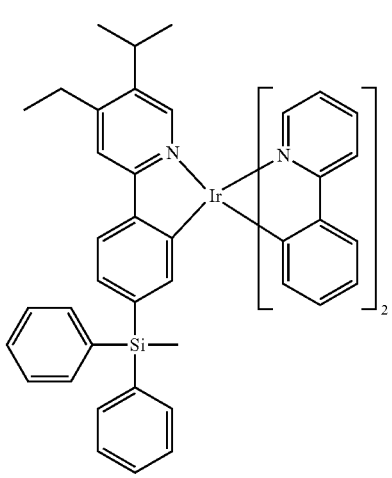
Compound 23
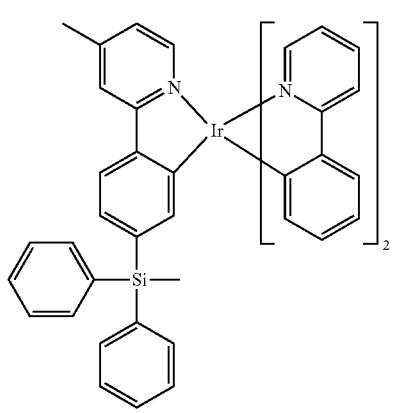
Compound 26
Compound 27
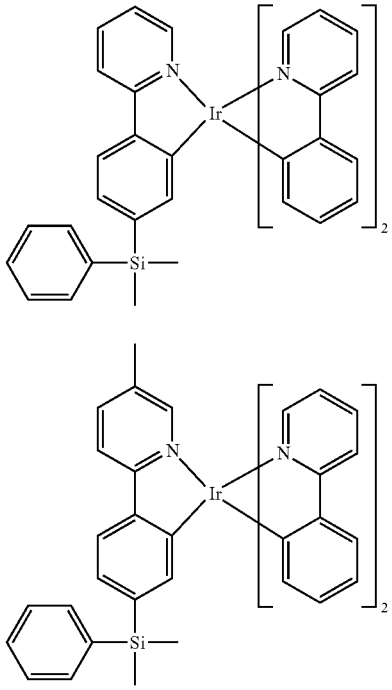

-continued
Compound 28
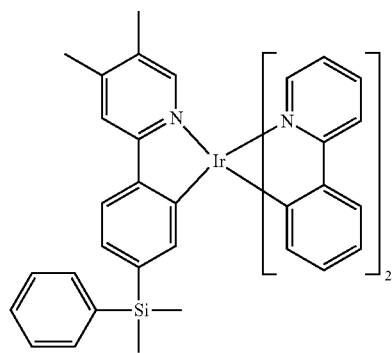
Compound 29
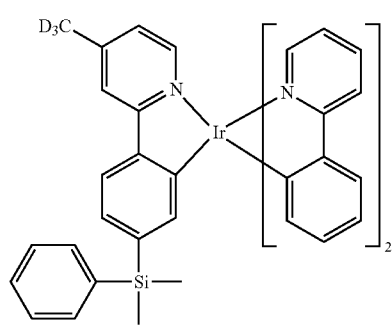
Compound 30
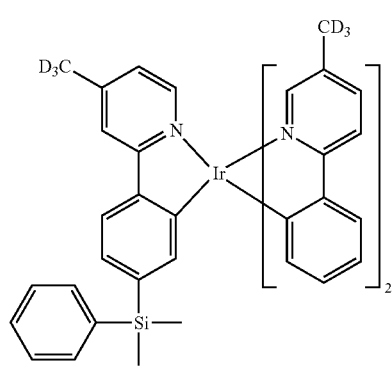
Compound 31
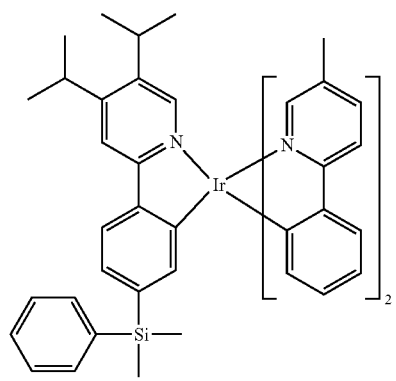
-continued
Compound 32
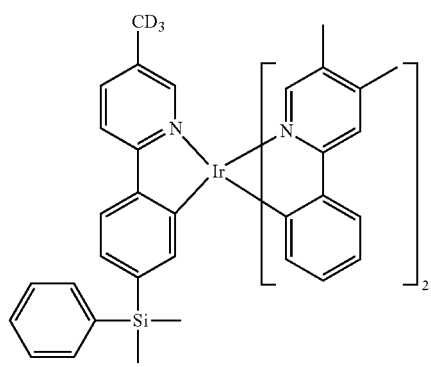
Compound 33
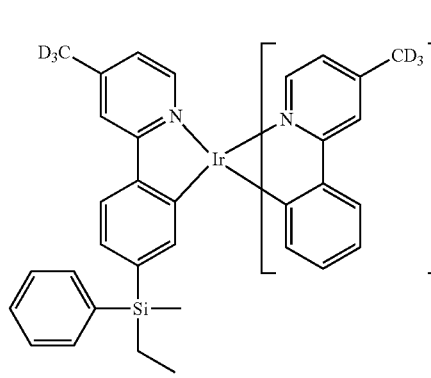
Compound 34
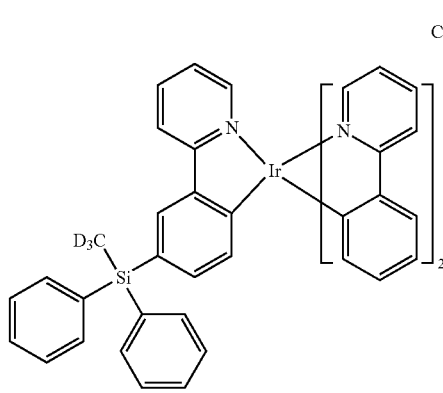
Compound 35
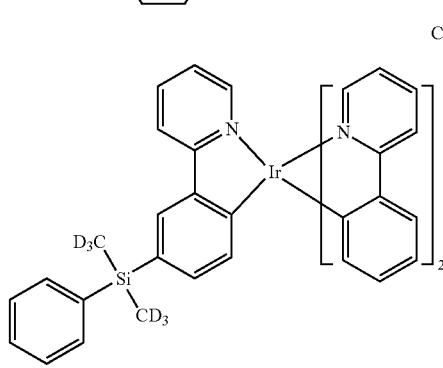

-continued

Compound 36

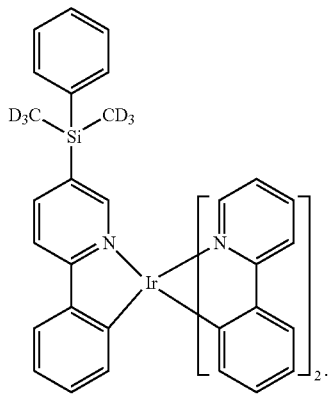

In one embodiment, a first device is provided. The first device comprises a first organic light emitting device, further comprising: an anode, a cathode, and an organic layer, disposed between the anode and the cathode, comprising a compound having the formula $M(L_1)_m(L_2)_n$. Ligand $L_1$ is a first ligand having the formula:

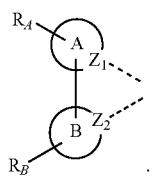

Formula I

Ligand $L_2$ is a second ligand having the formula:

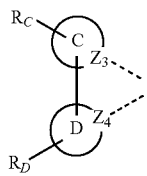

Formula II $L_1$ is different from $L_2$. A, B, C, and D are each independently a 5 or 6-membered carbocyclic or heterocyclic ring, and $Z_1$, $Z_2$, $Z_3$, and $Z_4$ are each independently selected from the group consisting of C or N. $R_A$, $R_B$, $R_c$ and $R_D$ each represent mono, di, tri, or tetra substitutions or no substitution, and any two adjacent substituents are optionally joined together to form a ring, which may be further substituted. At least one of $R_A$, $R_B$, $R_C$, and $R_D$ is $SiR_1R_2R_3$, wherein at least one of $R_1$, $R_2$, and $R_3$ is aryl or heteroaryl, which may be further substituted.

Each of $R_A$, $R_B$, $R_C$, $R_D$, $R_1$, $R_2$, and $R_3$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

M is a metal, m is an integer of at least 1, n is an integer of at least 1, and m+n is the maximum number of ligands that may be attached to metal M. Each $L_1$ and $L_2$ may be optionally linked with each other to comprise a tetradentate, or hexadentate ligand.

In one embodiment, the first device is a consumer product.

In one embodiment, the first device is an organic light-emitting device.

In one embodiment, the first device comprises a lighting panel.

In one embodiment, the organic layer is an emissive layer and the compound is an emissive dopant.

In one embodiment, the organic layer is an emissive layer and the compound is a non-emissive dopant.

In one embodiment, the organic layer further comprises a host.

In one embodiment, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=C_nH_{2n+1}$, $C\equiv CHC_nH_{2n+1}$, $Ar_1$, $Ar_1-Ar_2$, $C_nH_{2n}-Ar_1$, or no substitution, wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In one embodiment, the host is selected from the group consisting of:

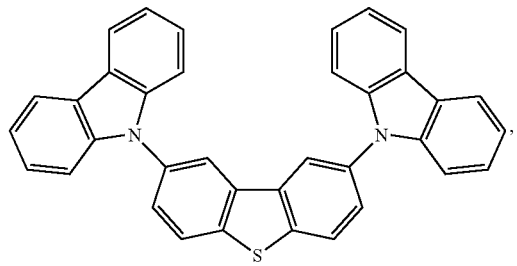

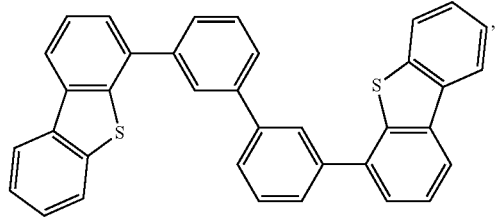

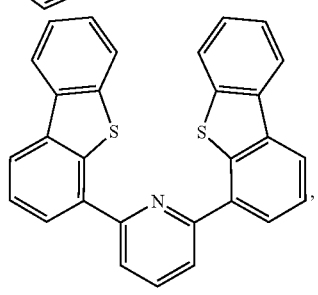

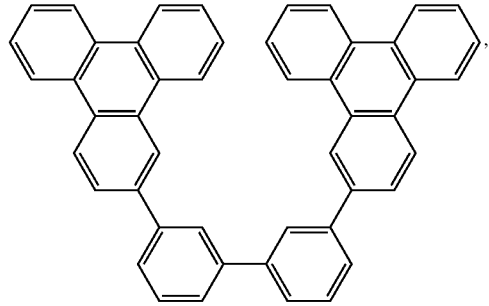

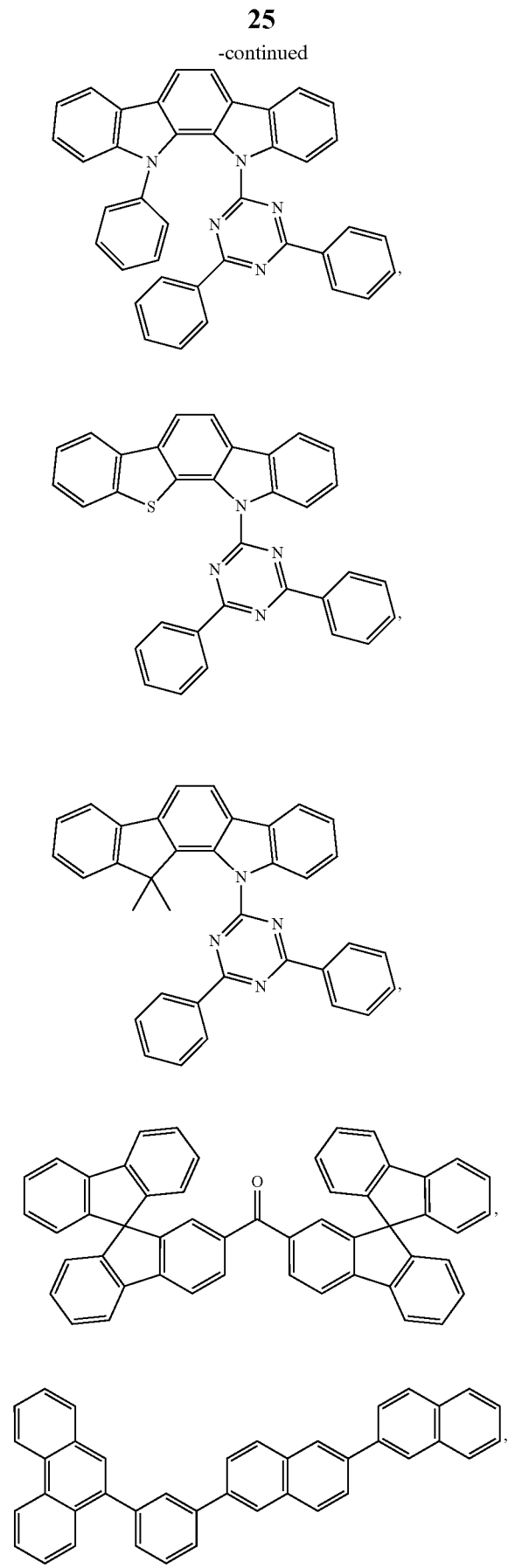

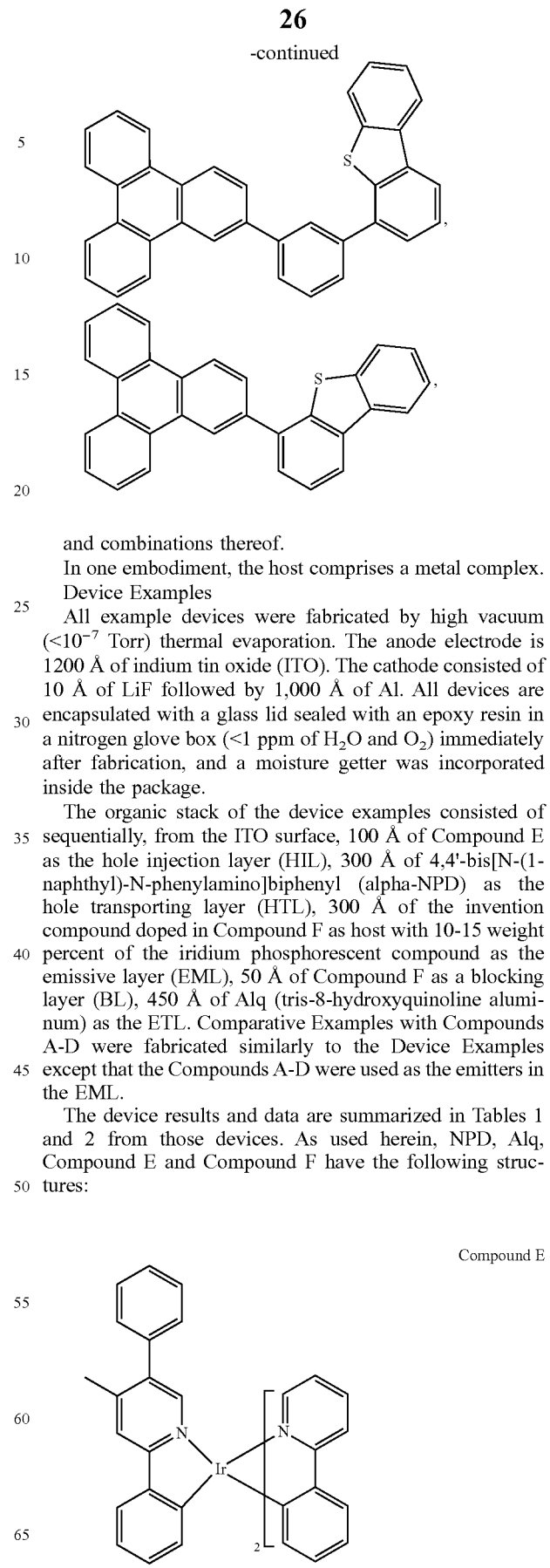

and combinations thereof.

In one embodiment, the host comprises a metal complex.

Device Examples

All example devices were fabricated by high vacuum (<10$^{-7}$ Torr) thermal evaporation. The anode electrode is 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of H$_2$O and O$_2$) immediately after fabrication, and a moisture getter was incorporated inside the package.

The organic stack of the device examples consisted of sequentially, from the ITO surface, 100 Å of Compound E as the hole injection layer (HIL), 300 Å of 4,4'-bis[N-(1-naphthyl)-N-phenylamino]biphenyl (alpha-NPD) as the hole transporting layer (HTL), 300 Å of the invention compound doped in Compound F as host with 10-15 weight percent of the iridium phosphorescent compound as the emissive layer (EML), 50 Å of Compound F as a blocking layer (BL), 450 Å of Alq (tris-8-hydroxyquinoline aluminum) as the ETL. Comparative Examples with Compounds A-D were fabricated similarly to the Device Examples except that the Compounds A-D were used as the emitters in the EML.

The device results and data are summarized in Tables 1 and 2 from those devices. As used herein, NPD, Alq, Compound E and Compound F have the following structures:

Compound F

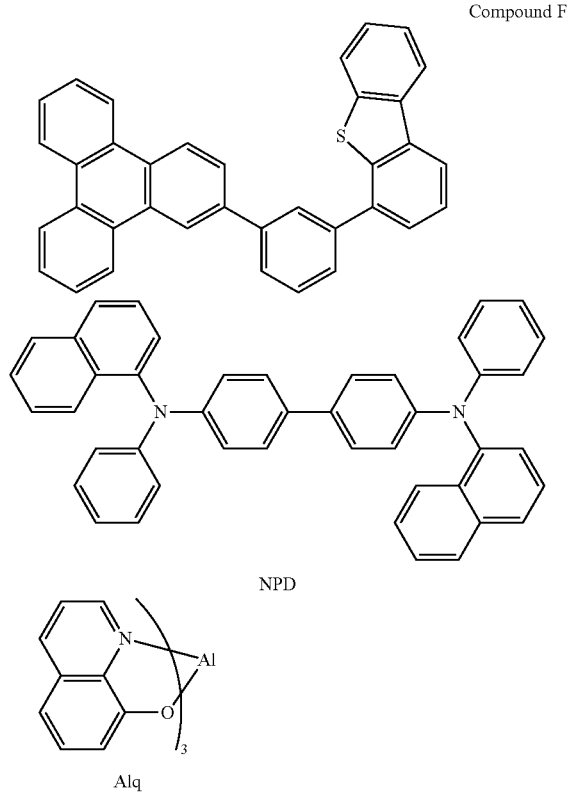

NPD

Alq

Compound A

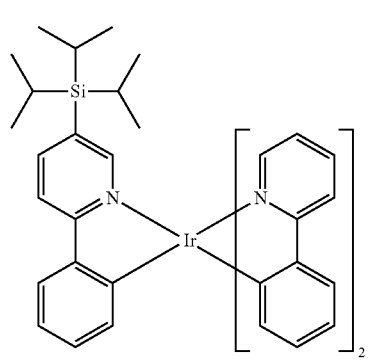

Compound B

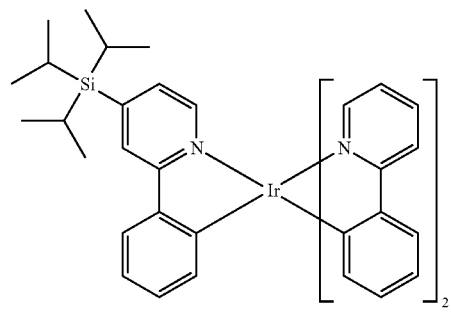

Compound C

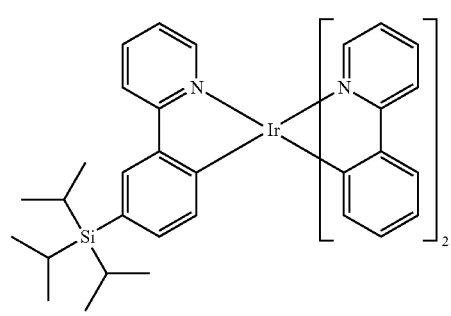

Compound D

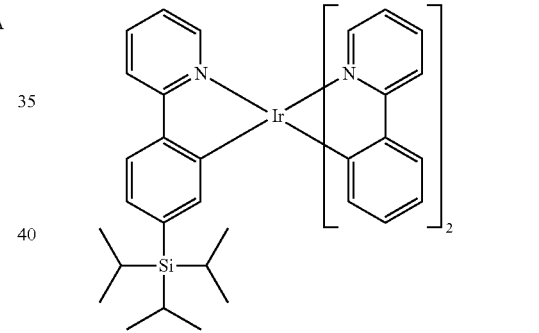

TABLE 1

Device Structures of inventive compounds and comparative compounds

| Example | HIL | HTL | EML (300 Å, doping %) | | BL | ETL |
|---|---|---|---|---|---|---|
| Example 1 | Compound E 100 Å | NPD 300 Å | Compound F | Compound 1 15% | Compound F 50 Å | Alq 450 Å |
| Example 2 | Compound E 100 Å | NPD 300 Å | Compound F | Compound 2 15% | Compound F 50 Å | Alq 450 Å |
| Example 3 | Compound E 100 Å | NPD 300 Å | Compound F | Compound 3 15% | Compound F 50 Å | Alq 450 Å |
| Example 4 | Compound E 100 Å | NPD 300 Å | Compound F | Compound 4 15% | Compound F 50 Å | Alq 450 Å |
| Example 5 | Compound E 100 Å | NPD 300 Å | Compound F | Compound 5 15% | Compound F 50 Å | Alq 450 Å |
| Comparative Example 1 | Compound E 100 Å | NPD 300 Å | Compound F | Compound A 15% | Compound F 50 Å | Alq 450 Å |
| Comparative Example 2 | Compound E 100 Å | NPD 300 Å | Compound F | Compound C 15% | Compound F 50 Å | Alq 450 Å |
| Comparative Example 3 | Compound E 100 Å | NPD 300 Å | Compound F | Compound D 15% | Compound F 50 Å | Alq 450 Å |

TABLE 2

VTE device results

| | x | y | $\lambda_{max}$ (nm) | FWHM (nm) | Voltage (V) | LE (cd/A) | EQE (%) | PE (lm/W) | $L_0$ (nits) | LT80 % (h) |
|---|---|---|---|---|---|---|---|---|---|---|
| Example 1 | 0.394 | 0.585 | 540 | 74 | 5.2 | 71.5 | 19.7 | 43.1 | 21,716 | 355 |
| Example 2 | 0.427 | 0.559 | 550 | 76 | 5.9 | 67.4 | 19.3 | 35.8 | 21,131 | 369 |
| Example 3 | 0.317 | 0.617 | 518 | 76 | 6.9 | 31.2 | 8.8 | 14.3 | 10,387 | 172 |
| Example 4 | 0.315 | 0.621 | 518 | 74 | 6.8 | 37.2 | 10.5 | 17.1 | 12,390 | 234 |
| Example 5 | 0.38 | 0.594 | 534 | 74 | 7.3 | 35.1 | 9.7 | 15.1 | 11,294 | 377 |
| Comparative Example 1 | 0.339 | 0.617 | 524 | 72 | 5.2 | 55 | 14.2 | 33.4 | 17,608 | 2 |
| Comparative Example 2 | 0.324 | 0.619 | 520 | 74 | 7.1 | 27.9 | 7.8 | 12.4 | 10,271 | 25.4 |
| Comparative Example 3 | 0.357 | 0.607 | 530 | 72 | 8.1 | 22.4 | 6.1 | 8.7 | 8,494 | 3 |

Table 2 summarizes the performance of the devices. The driving voltage (V), luminous efficiency (LE), external quantum efficiency (EQE) and power efficiency (PE) were measured at 1000 nits, while the lifetime ($LT_{80\%}$) was defined as the time required for the device to decay to 80% of its initial luminance ($L_0$) under a constant current density of 40 mA/cm$^2$.

Comparative compounds A-D have triisopropylsilyl substitution at various positions. The inventive compounds have at least one aryl group attached to the silyl substituent. The advantages of aryl-silyl substitution over trialkyl-silyl substitution are very clear from the device data shown above in Table 2. The first comparison is Comparative example 1 (Compound A) vs inventive example 1 (Compound 1). Compound B decomposed upon sublimation therefore no device could be made. The most obvious unexpected results are the yellow color of Compounds 1 and 2 and the striking device lifetime difference. Compound 1 and 2 represent a new class of yellow phosphorescent emitters useful in both display and lighting applications.

Continuing with the first comparison, Compound 1 has comparable emission broadness to compound A as measured by FWHM (full width at half maximum) (74 nm vs 72 nm). Both require the same voltage (5.2V), however Compound 1 produces more efficient devices than Compound A in every category: LE (71.5 cd/A vs. 55 cd/A), EQE (19.7% vs. 14.2%) and PE (43.1 lm/W vs. 33.4 lm/W) respectively. The initial luminance for Compound 1 (21,716 nits) was higher than for Compound A (17,608 nits) while the $LT_{80\%}$ for Compound 1 was 355 h vs. 2 h for Compound A.

Comparison of Compound 3 (Example 3) and Compound 4 (Example 4) vs Compound C (comparative example 2). Both Compound 3 and 4 display $\lambda_{max}$ at 518 nm vs 520 nm for Compound C. The broadness of the emission, 76 nm and 74 nm, for Compounds 3 and 4 respectively, is comparable to the 74 nm for Compound C. The voltage for Compounds 3 and 4 is slightly lower (6.9 V, 6.8 V) than that for Compound C (7.1 V). Compounds 3 and 4 produce devices with superior efficiencies in every category relative to devices containing Compound C: LE (31.2, 37.2 cd/A vs. 27.9 cd/A), EQE (8.8%, 10.5% vs. 7.8%), PE (14.3, 17.1 lm/W vs. 12.4 lm/W). The initial luminance for Compounds 3 and 4 (10,387, 12,390 nits) were each higher than that of Compound C (10,271 nits). The $LT_{80\%}$ for Compounds 3 and 4 were 172 and 234 h respectively compared to 25.4 h for Compound C.

The final comparison is between Compound 5 (Example 5) and Compound D (comparative example 3). The broadness of the emission is comparable (74 nm vs. 72 nm). The voltage for Compound 5 is lower (7.3 vs. 8.1 V) than for Compound D. Compound 5 produces devices with superior efficiency in all categories measured relative to devices made with Compound D: LE (35.1 vs. 22.4 cd/A), EQE (9.6 vs. 6.1%), PE (15.1 vs. 8.7 lm/W). The initial luminance of Compound 5 greatly exceeds that of Compound D (11,294 vs. 8494 nits). Finally, the $LT_{80\%}$ of Compound 5 is 377 h while that of Compound D is 3 h. The other direct comparisons are comparative example 2 (Compound C) vs. inventive examples 3 (Compound 3) and 4 (Compound 4) and finally, comparative example 3 (Compound D) vs. inventive example 5 (Compound 5).

As can be seen from the table, every compound of Formula I requires less voltage than the comparative compound. Additionally the inventive compounds, without exception, produced more efficient devices in all categories, including LE, EQE, PE. The initial luminance of the inventive compounds outperformed that of the comparative compounds in all observed cases. Finally, and perhaps most striking of all, is the difference in the $LT_{80\%}$ values between the comparative compounds and the inventive compounds. This difference in $LT_{80\%}$ values ranges from 6.8 times (Example 3 vs. Comparative Example 2) to more than 177 times (Example 1 vs. Comparative Example 1).

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphoric acid and sliane derivatives; a metal oxide derivative, such as MoO$_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

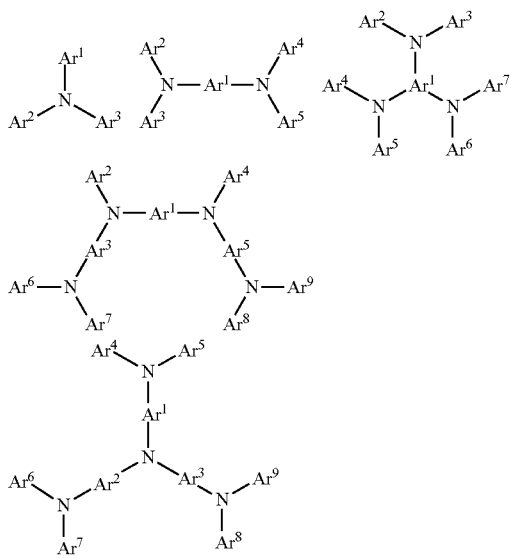

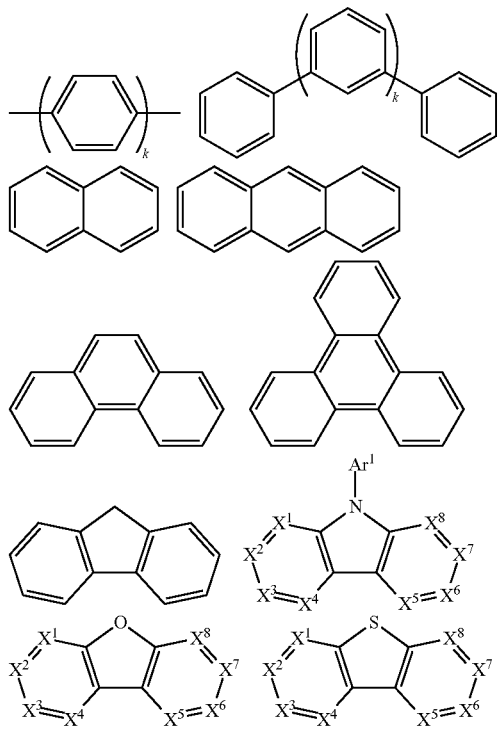

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of k is an integer from 1 to 20; $X^1$ to $X^8$ is C (including CH) or N; $Ar^1$ has the same group defined above.

Examples of metal complexes used in HIL or HTL include, but not limit to the following general formula:

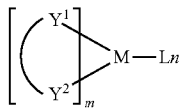

M is a metal, having an atomic weight greater than 40; $(Y^1-Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.

In another aspect, $(Y^1-Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

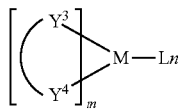

M is a metal; ($Y^3$—$Y^4$) is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

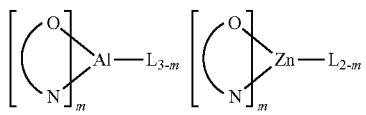

(O—N) is a bidentate ligand, having metal coordinated to atoms O and N.

In another aspect, M is selected from Ir and Pt.

In a further aspect, ($Y^3$—$Y^4$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, triazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

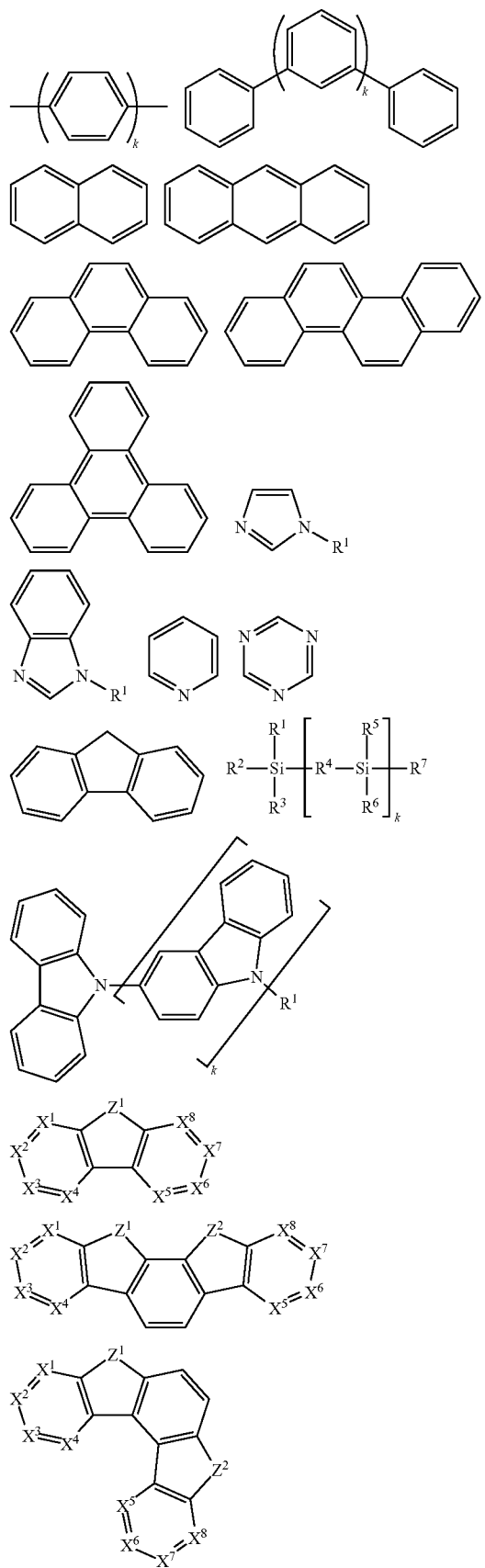

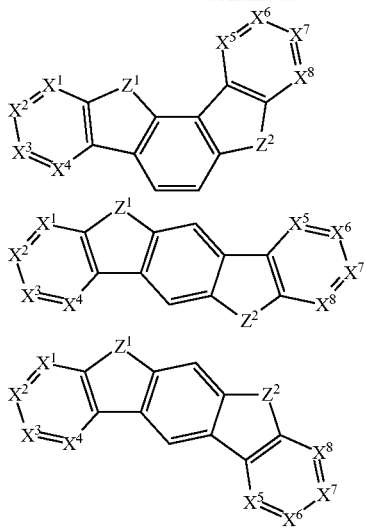

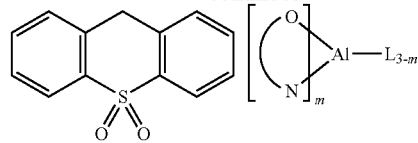

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

$X^1$ to $X^8$ is selected from C (including CH) or N.

$Z^1$ and $Z^2$ is selected from $NR^1$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

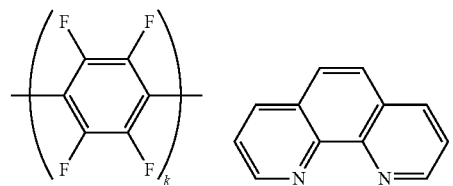

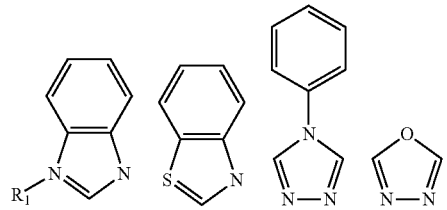

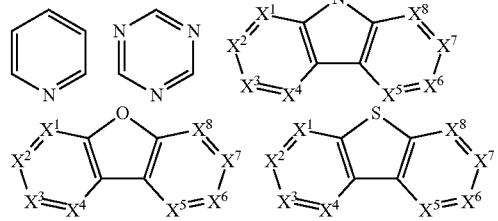

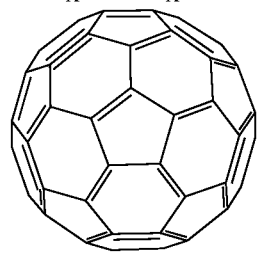

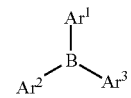

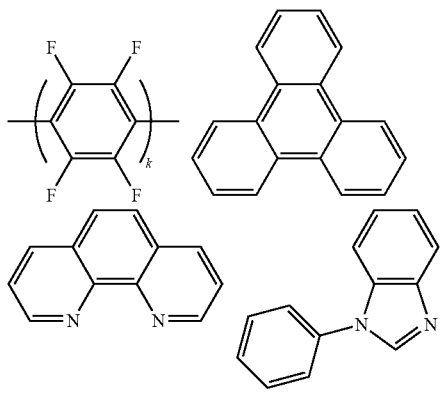

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

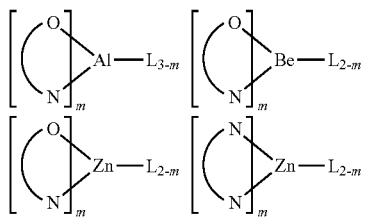

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 3 below. Table 3 lists non-limiting classes of materials, non-limiting examples of compounds for each class, and references that disclose the materials.

TABLE 3

| MATERIAL | EXAMPLES OF MATERIAL | PUBLICATIONS |
|---|---|---|
| Hole injection materials | | |
| Phthalocyanine and porphryin compounds | 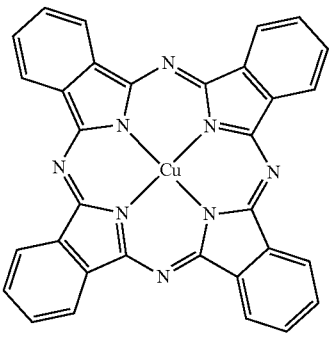 | Appl. Phys. Lett. 69, 2160 (1996) |
| Starburst triarylamines | 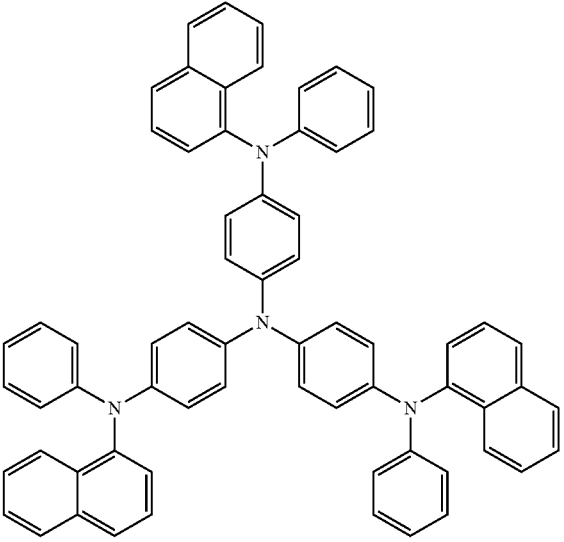 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | —$[CH_xF_y]_n$— | Appl. Phys. Lett. 78, 673 (2001) |

TABLE 3-continued
| MATERIAL | EXAMPLES OF MATERIAL | PUBLICATIONS |
| --- | --- | --- |
| Conducting polymers (e.g., PEDOT:PSS, polyaniline, polypthiophene) | 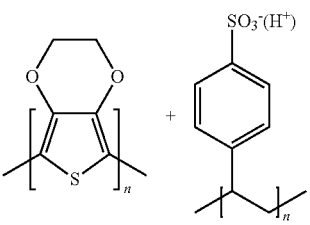 | Synth. Met. 87, 171 (1997)<br>WO2007002683 |
| Phosphonic acid and sliane SAMs | 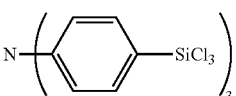 | US20030162053 |
| Triarylamine or polythiophene polymers with conductivity dopants | 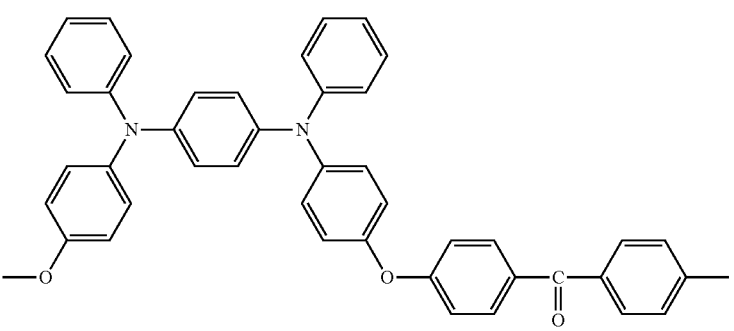 and 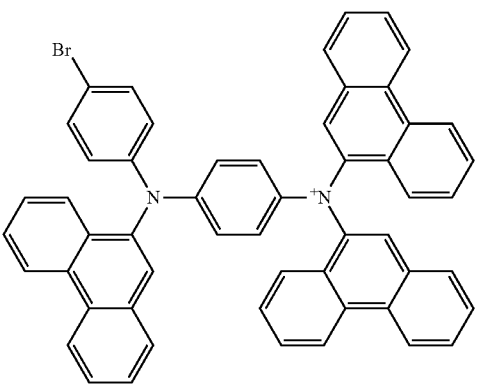 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 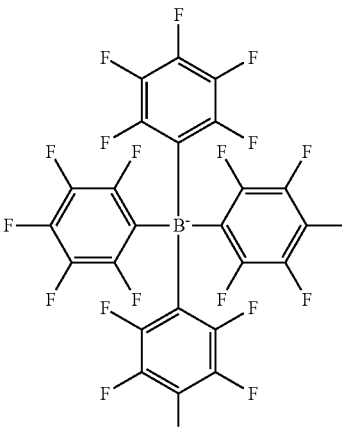 | EP1725079A1 |

TABLE 3-continued
| MATERIAL | EXAMPLES OF MATERIAL | PUBLICATIONS |
|---|---|---|
| Organic compounds with conductive inorganic compounds, such as molybdenum and tungsten oxides | 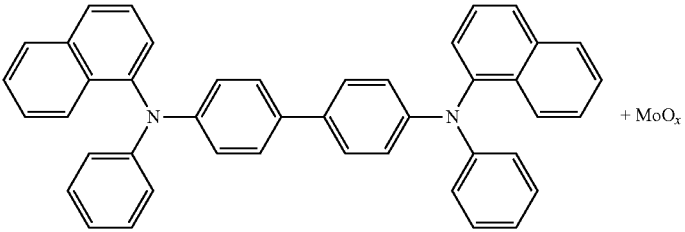 [SMILES: c1ccc(N(c2ccc(-c3ccc(N(c4ccccc4)c4cccc5ccccc45)cc3)cc2)c2cccc3ccccc23)cc1] + MoO$_x$ | US20050123751<br>SID Symposium Digest, 37, 923 (2006)<br>WO2009018009 |
| n-type semiconducting organic complexes | 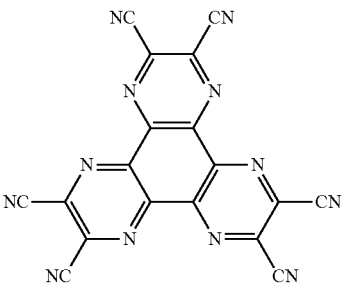 [SMILES: N#Cc1nc2c3nc(C#N)c(C#N)nc3c3nc(C#N)c(C#N)nc3c2nc1C#N] | US20020158242 |
| Metal organometallic complexes | 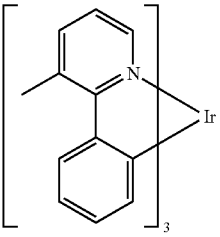 | US20060240279 |
| Cross-linkable compounds | 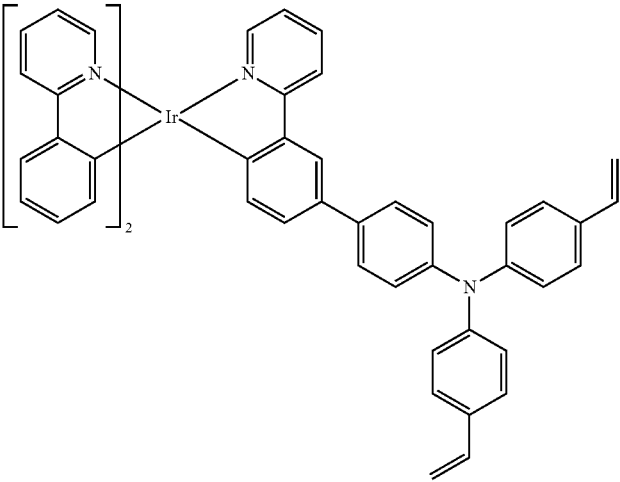 | US20080220265 |

TABLE 3-continued

| MATERIAL | EXAMPLES OF MATERIAL | PUBLICATIONS |
|---|---|---|
| Polythiophene based polymers and copolymers | | WO 2011075644<br>EP2350216 |

Hole transporting materials

| | | |
|---|---|---|
| Triarylamines (e.g., TPD, α-NPD) | | Appl. Phys. Lett. 51, 913 (1987) |
| | | U.S. Pat. No. 5,061,569 |
| | | EP650955 |

TABLE 3-continued
| MATERIAL | EXAMPLES OF MATERIAL | PUBLICATIONS |
|---|---|---|
| | 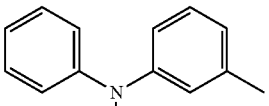 | J. Mater. Chem. 3, 319 (1993) |
| | 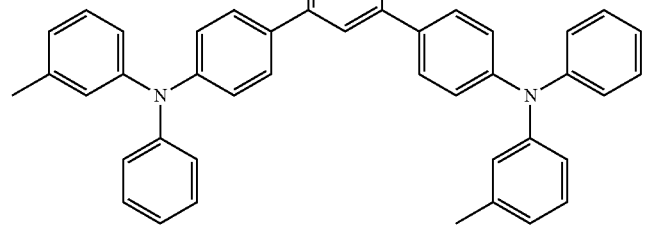 | Appl. Phys. Lett. 90, 183503 (2007) |
| | 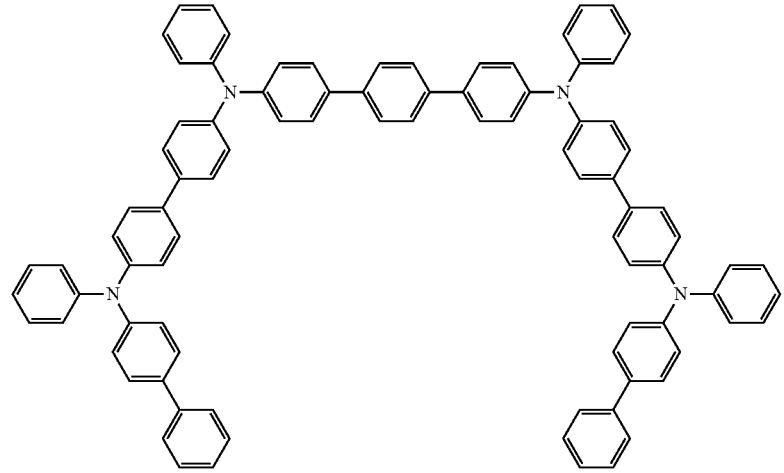 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 3-continued

| MATERIAL | EXAMPLES OF MATERIAL | PUBLICATIONS |
| --- | --- | --- |
| Triaylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |
| Indolocarbazoles | | Synth. Met. 111, 421 (2000) |

TABLE 3-continued

| MATERIAL | EXAMPLES OF MATERIAL | PUBLICATIONS |
| --- | --- | --- |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |
| Metal 8-hydroxy-quinolates (e.g., Alq3, BAlq) | | Nature 395, 151 (1998) |
| | | US20060202194 |

| MATERIAL | EXAMPLES OF MATERIAL | PUBLICATIONS |
|---|---|---|
| | 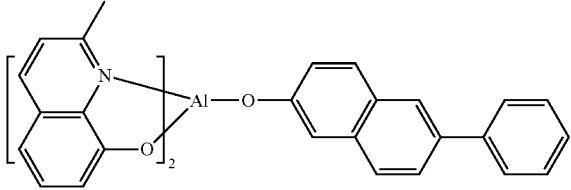 | WO2005014551 |
| | 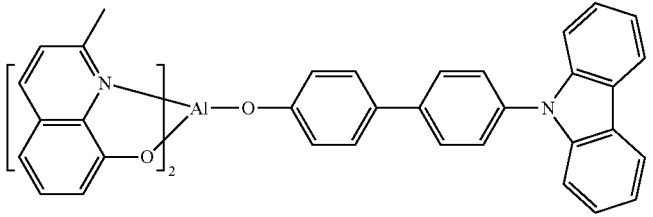 | WO2006072002 |
| Metal phenoxybenzothiazole compounds | 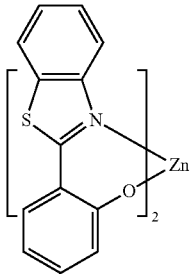 | Appl. Phys. Lett. 90, 123509 (2007) |
| Conjugated oligomers and polymers (e.g., polyfluorene) | 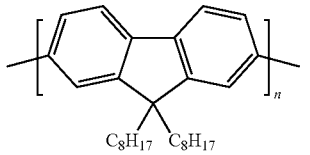 | Org. Electron. 1, 15 (2000) |
| Aromatic fused rings | 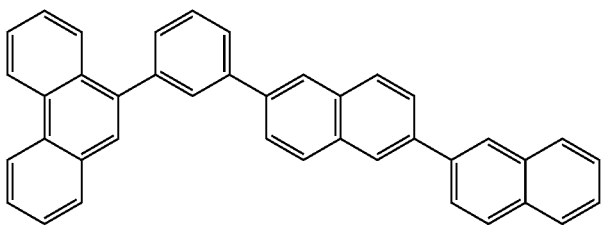 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 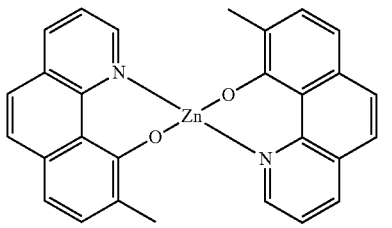 | WO2010056066 |

TABLE 3-continued

| MATERIAL | EXAMPLES OF MATERIAL | PUBLICATIONS |
|---|---|---|
| Chrysene based compounds | | WO2011086863 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 3-continued

| MATERIAL | EXAMPLES OF MATERIAL | PUBLICATIONS |
|---|---|---|
| | | US20060280965 |
| | | WO2009021126 |
| Poly-fused heteroaryl compounds | | US20090309488<br>US20090302743<br>US20100012931 |
| Donor acceptor type molecules | | WO2008056746 |
| | | WO2010107244 |

TABLE 3-continued
| MATERIAL | EXAMPLES OF MATERIAL | PUBLICATIONS |
|---|---|---|
| Aza-carbazole/DBT/DBF | 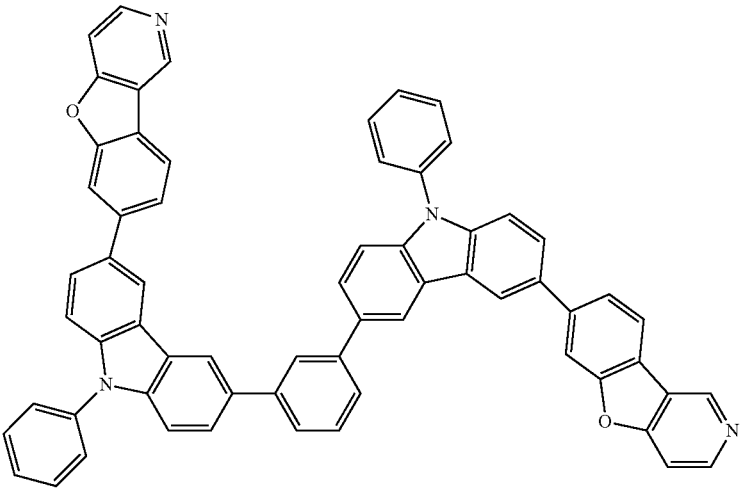 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 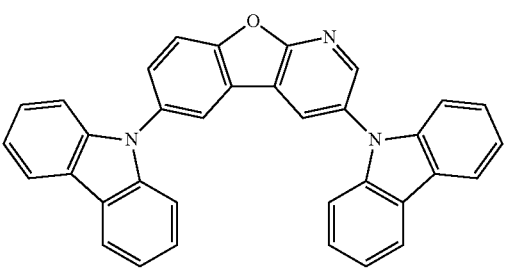 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 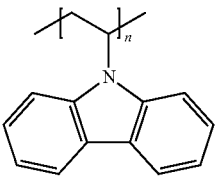 | Appl. Phys. Lett. 77, 2280 (2000) |
| Spirofluorene compounds | 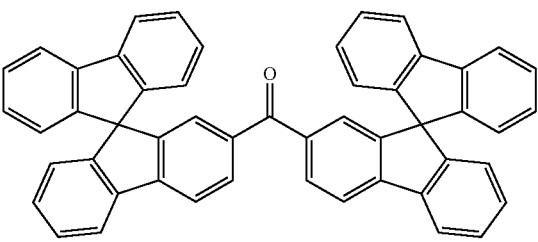 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 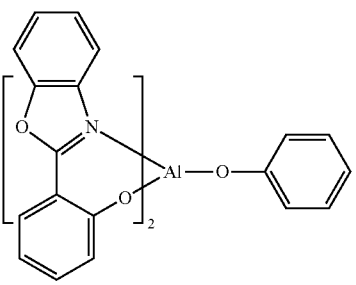 | WO2005089025 |

TABLE 3-continued

| MATERIAL | EXAMPLES OF MATERIAL | PUBLICATIONS |
|---|---|---|
| | | WO2006132173 |
| | | JP200511610 |
| Spirofluorene-carbazole compounds | | JP2007254297 |
| | | JP2007254297 |
| Indolocabazoles | | WO2007063796 |

TABLE 3-continued
| MATERIAL | EXAMPLES OF MATERIAL | PUBLICATIONS |
|---|---|---|
| | 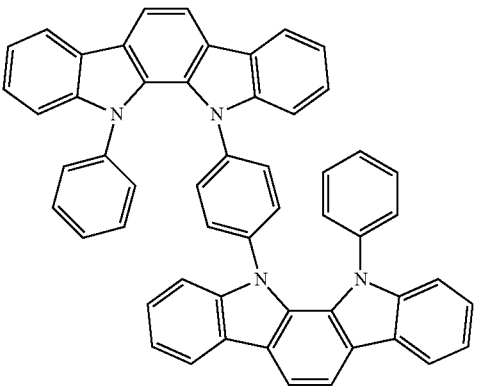 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 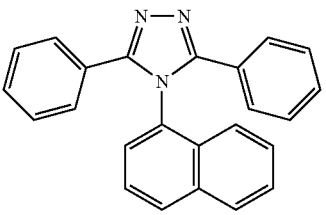 [SMILES: c1ccc(-c2nnc(-c3ccccc3)n2-c2cccc3ccccc23)cc1] | J. Appl. Phys. 90, 5048 (2001) |
| | 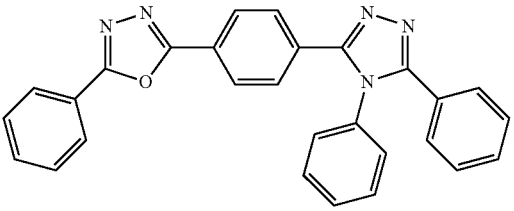 [SMILES: c1ccc(-c2nnc(-c3ccc(-c4nnc(-c5ccccc5)n4-c4ccccc4)cc3)o2)cc1] | WO2004107822 |
| Tetraphenylene complexes | 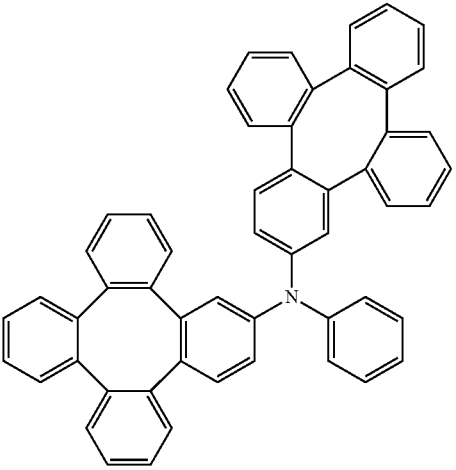 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 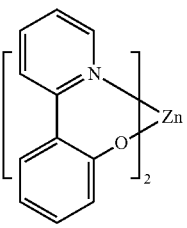 | WO2005030900 |

TABLE 3-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |ира
| Blue hosts | | |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

TABLE 3-continued
| MATERIAL | EXAMPLES OF MATERIAL | PUBLICATIONS |
|---|---|---|
| | 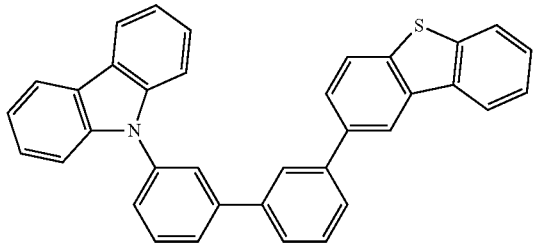 [SMILES: c1cc(-c2cccc(-n3c4ccccc4c4ccccc43)c2)cc(-c2ccc3sc4ccccc4c3c2)c1] | US20090030202, US20090017330 |
| | 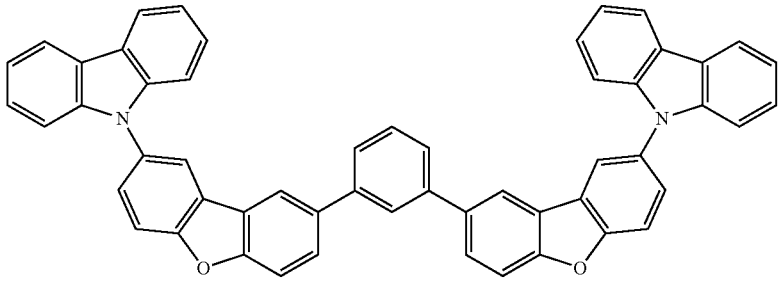 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 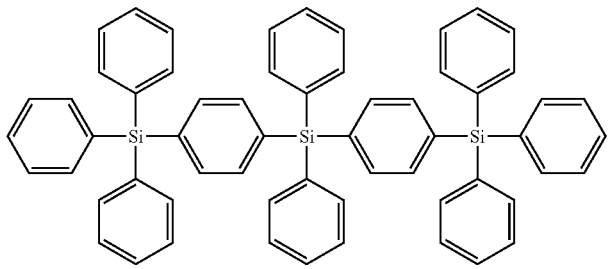 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 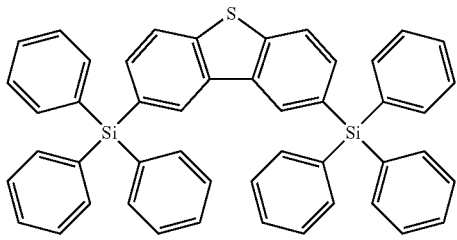 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 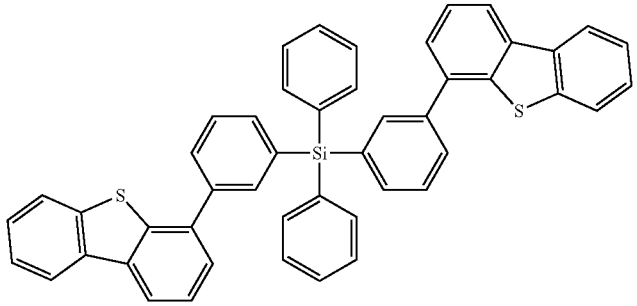 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 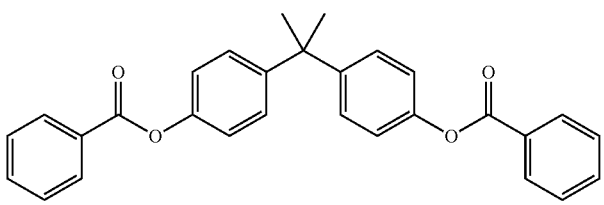 [SMILES: CC(C)(c1ccc(OC(=O)c2ccccc2)cc1)c1ccc(OC(=O)c2ccccc2)cc1] | WO2006100298 |

TABLE 3-continued

| MATERIAL | EXAMPLES OF MATERIAL | PUBLICATIONS |
|---|---|---|
| Carbazole linked by non-conjugated groups | | US20040115476 |
| Aza-carbazoles | | US20060121308 |
| High triplet metal organometallic complex | | U.S. Pat. No. 7,154,114 |
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |

TABLE 3-continued

| MATERIAL | EXAMPLES OF MATERIAL | PUBLICATIONS |
|---|---|---|
| | [Ir complex structure] | US2006835469 |
| | [Ir complex structure] | US2006835469 |
| | [Ir complex structure] | US20060202194 |
| | [Ir complex structure] | US20060202194 |

TABLE 3-continued

| MATERIAL | EXAMPLES OF MATERIAL | PUBLICATIONS |
|---|---|---|
| | | US20070087321 |
| | | US20080261076<br>US20100090591 |
| | | US20070087321 |
| | | Adv. Mater. 19, 739 (2007) |
| | | WO2009100991 |

TABLE 3-continued
| MATERIAL | EXAMPLES OF MATERIAL | PUBLICATIONS |
|---|---|---|
| | 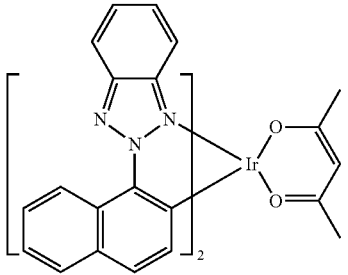 | WO2008101842 |
| | 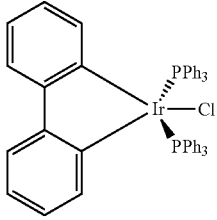 | U.S. Pat. No. 7,232,618 |
| Platinum(II) organometallic complexes | 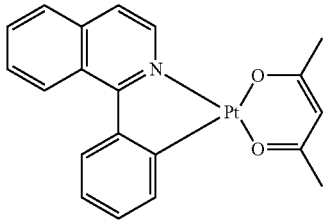 | WO2003040257 |
| | 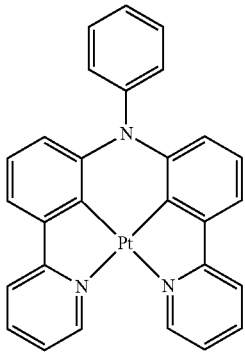 | US20070103060 |
| Osminum(III) complexes | 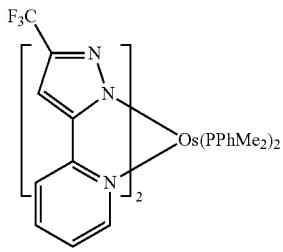 | Chem. Mater. 17, 3532 (2005) |

TABLE 3-continued

| MATERIAL | EXAMPLES OF MATERIAL | PUBLICATIONS |
| --- | --- | --- |
| Ruthenium(II) complexes | | Adv. Mater. 17, 1059 (2005) |
| Rhenium (I), (II), and (III) complexes | | US20050244673 |

Green dopants

| | | |
| --- | --- | --- |
| Iridium(III) organometallic complexes | and its derivatives | Inorg. Chem. 40, 1704 (2001) |
| | | US20020034656 |

TABLE 3-continued
| MATERIAL | EXAMPLES OF MATERIAL | PUBLICATIONS |
|---|---|---|
| | 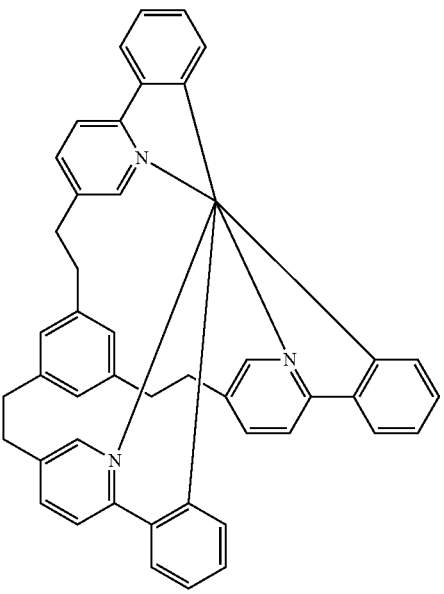 | U.S. Pat. No. 7,332,232 |
| | 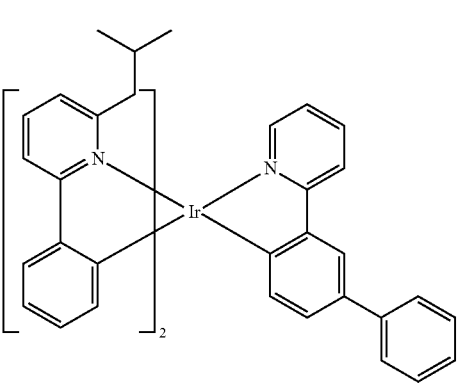 | US20090108737 |
| | 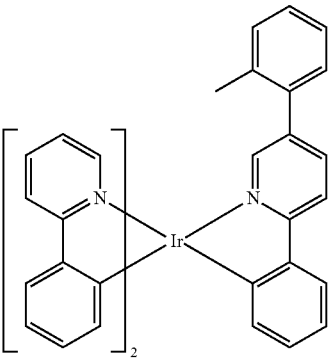 | WO2010028151 |

TABLE 3-continued
| MATERIAL | EXAMPLES OF MATERIAL | PUBLICATIONS |
|---|---|---|
| | 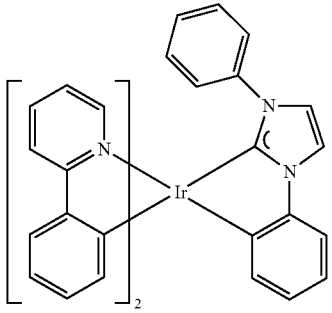 | EP1841834B |
| | 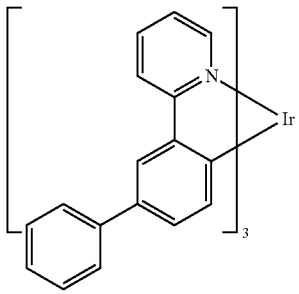 | US20060127696 |
| | 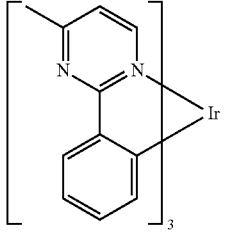 | US20090039776 |
| | 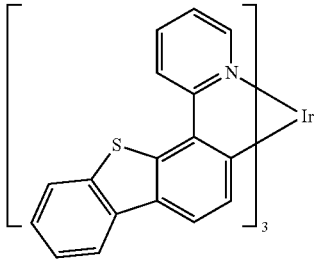 | U.S. Pat. No. 6,921,915 |
| | 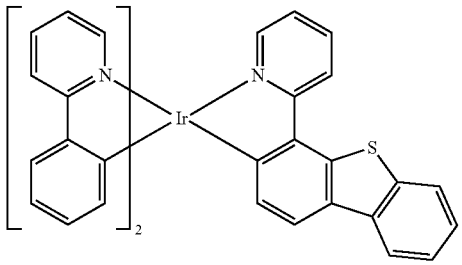 | US20100244004 |

TABLE 3-continued

| MATERIAL | EXAMPLES OF MATERIAL | PUBLICATIONS |
|---|---|---|
| | | U.S. Pat. No. 6,687,266 |
| | | Chem. Mater. 16, 2480 (2004) |
| | | US20070190359 |
| | | US 20060008670<br>JP2007123392 |
| | | WO2010086089,<br>WO2011044988 |
| | | Adv. Mater. 16, 2003 (2004) |

TABLE 3-continued

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090165846 |
| | | US20080015355 |
| | | US20010015432 |
| | | US20100295032 |

TABLE 3-continued

| MATERIAL | EXAMPLES OF MATERIAL | PUBLICATIONS |
|---|---|---|
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE 3-continued

| MATERIAL | EXAMPLES OF MATERIAL | PUBLICATIONS |
|---|---|---|
| | | US20060263635 |
| | | US20060182992<br>US20070103060 |
| Cu complexes | | WO2009000673 |
| | | US20070111026 |

TABLE 3-continued
| MATERIAL | EXAMPLES OF MATERIAL | PUBLICATIONS |
|---|---|---|
| Gold complexes | 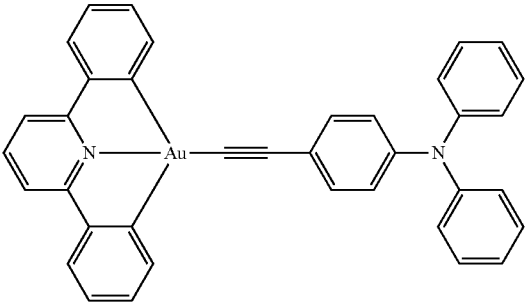 | Chem. Commun. 2906 (2005) |
| Rhenium(III) complexes | 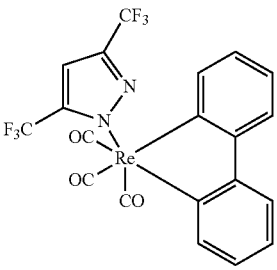 | Inorg. Chem. 42, 1248 (2003) |
| Osmium(II) complexes | 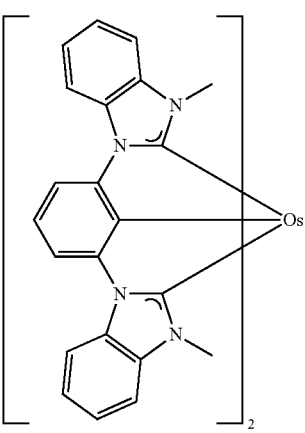 | U.S. Pat. No. 7,279,704 |
| Deuterated organometallic complexes | 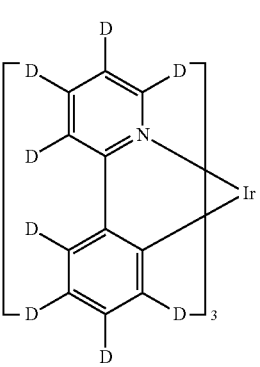 | US20030138657 |

TABLE 3-continued
| MATERIAL | EXAMPLES OF MATERIAL | PUBLICATIONS |
|---|---|---|
| Organometallic complexes with two or more metal centers | 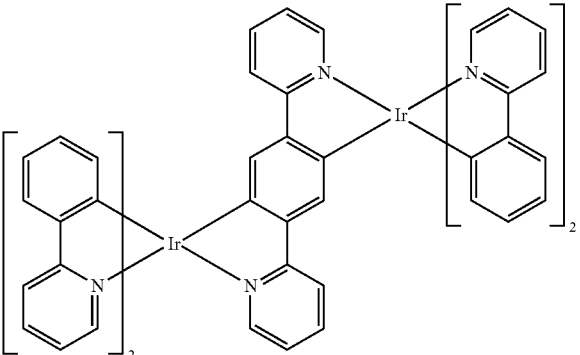 | US20030152802 |
| | 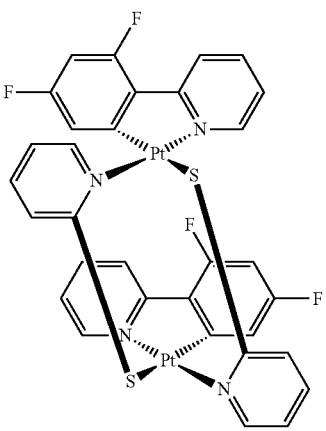 | U.S. Pat. No. 7,090,928 |
| Blue dopants | | |
| Iridium(III) organometallic complexes | 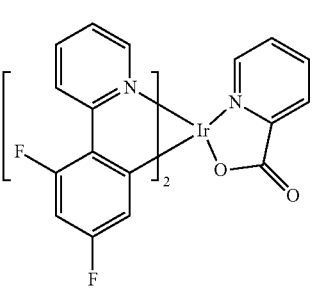 | WO2002002714 |
| | 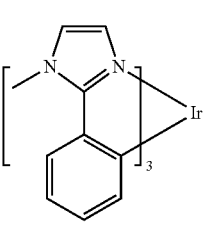 | WO2006009024 |
| | 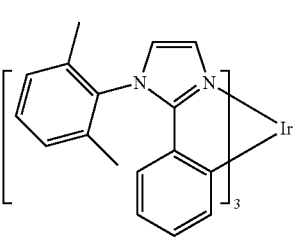 | US20060251923<br>US20110057559<br>US20110204333 |

TABLE 3-continued

| MATERIAL | EXAMPLES OF MATERIAL | PUBLICATIONS |
|---|---|---|
| | | U.S. Pat. No. 7,393,599, WO2006056418, US20050260441, WO2005019373 |
| | | U.S. Pat. No. 7,534,505 |
| | | WO2011051404 |
| | | U.S. Pat. No. 7,445,855 |
| | | US20070190359, US20080297033 US20100148663 |

TABLE 3-continued

| MATERIAL | EXAMPLES OF MATERIAL | PUBLICATIONS |
|---|---|---|
|  |  | U.S. Pat. No. 7,338,722 |
|  |  | US20020134984 |
|  |  | Angew. Chem. Int. Ed. 47, 1 (2008) |
|  |  | Chem. Mater. 18, 5119 (2006) |
|  |  | Inorg. Chem. 46, 4308 (2007) |

TABLE 3-continued

| MATERIAL | EXAMPLES OF MATERIAL | PUBLICATIONS |
|---|---|---|
| | [Ir complex with N-methylpyrazole-phenyl ligand]₃ | WO2005123873 |
| | [Ir complex with dimethylimidazole-naphthyl ligand]₃ | WO2005123873 |
| | [Ir complex with methylimidazole-phenylpyrrole ligand]₃ | WO2007004380 |
| | [Ir complex with pyridine-indole and phenyl-pyrazole-indazole ligands] | WO2006082742 |
| Osmium(II) complexes | [Os complex with benzimidazole carbene ligands]₂ | U.S. Pat. No. 7,279,704 |

TABLE 3-continued

| MATERIAL | EXAMPLES OF MATERIAL | PUBLICATIONS |
|---|---|---|
| | [Os complex with pyrazolyl-pyridine ligands and PPh₃] | Organometallics 23, 3745 (2004) |
| Gold complexes | Ph₂P–PPh₂ with Au–Cl groups | Appl. Phys. Lett. 74, 1361 (1999) |
| Platinum(II) complexes | [Pt complex with thiophene, pyrimidine, and tetrakis(pyrazolyl)borate ligands] | WO2006098120, WO2006103874 |
| Pt tetradentate complexes with at least one metal-carbene bond | [Pt tetradentate carbene complex] | U.S. Pat. No. 7,655,323 |
| Exciton/hole blocking layer materials | | |
| Bathocuprine compounds (e.g., BCP, BPhen) | [BCP structure] | Appl. Phys. Lett. 75, 4 (1999) |
| | [BPhen structure] | Appl. Phys. Lett. 79, 449 (2001) |
| Metal 8-hydroxy-quinolates (e.g., BAlq) | [BAlq structure] | Appl. Phys. Lett. 81, 162 (2002) |

TABLE 3-continued

| MATERIAL | EXAMPLES OF MATERIAL | PUBLICATIONS |
| --- | --- | --- |
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE 3-continued

| MATERIAL | EXAMPLES OF MATERIAL | PUBLICATIONS |
|---|---|---|
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |
| Electron transporting materials | | |
| Anthracene-benzoimidazole compounds | | WO2003060956 |
| | | US20090179554 |

| MATERIAL | EXAMPLES OF MATERIAL | PUBLICATIONS |
|---|---|---|
| Aza triphenylene derivatives | 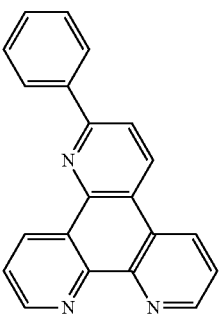 [SMILES: c1ccc(-c2ccc3c4cccnc4c4ncccc4c3n2)cc1] | US20090115316 |
| Anthracene-benzothiazole compounds | 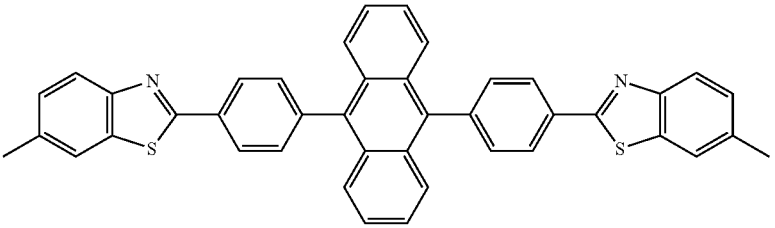 | Appl. Phys. Lett. 89, 063504 (2006) |
| Metal 8-hydroxy-quinolates (e.g., $Alq_3$, $Zrq_4$) | 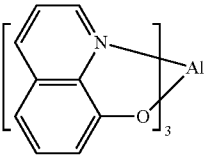 | Appl. Phys. Lett. 51, 913 (1987) U.S. Pat. No. 7,230,107 |
| Metal hydroxybenoquinolates | 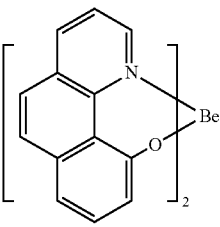 | Chem. Lett. 5, 905 (1993) |
| Bathocuprine compounds such as BCP, BPhen, etc | 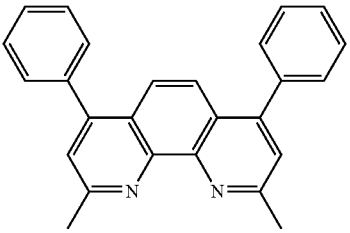 [SMILES: Cc1cc(-c2ccccc2)c2ccc3c(-c4ccccc4)cc(C)nc3c2n1] | Appl. Phys. Lett. 91, 263503 (2007) |
| | 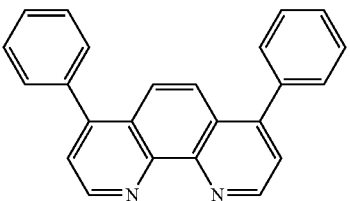 [SMILES: c1ccc(-c2ccnc3c2ccc2c(-c4ccccc4)ccnc23)cc1] | Appl. Phys. Lett. 79, 449 (2001) |

TABLE 3-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 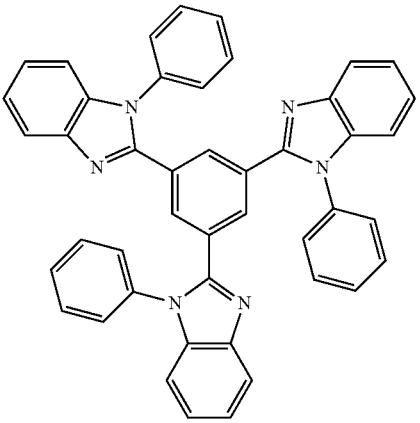 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 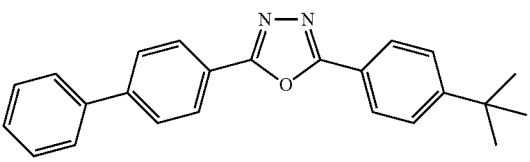 [SMILES: CC(C)(C)c1ccc(-c2nnc(-c3ccc(-c4ccccc4)cc3)o2)cc1] | Appl. Phys. Lett. 55, 1489 (1989) |
| | 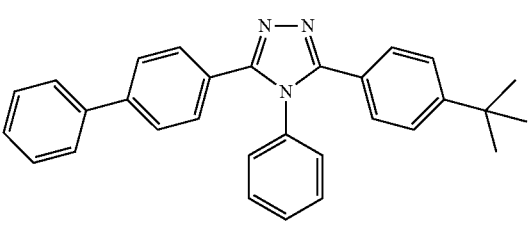 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 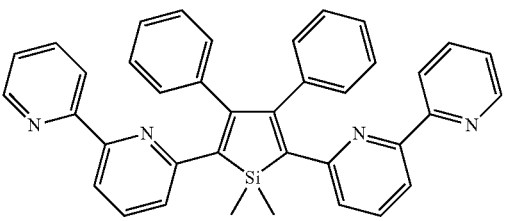 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 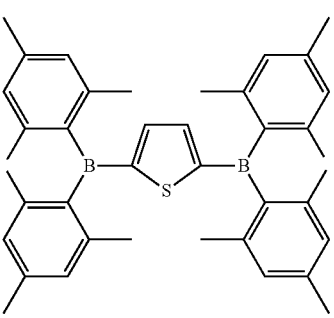 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |

TABLE 3-continued

| MATERIAL | EXAMPLES OF MATERIAL | PUBLICATIONS |
|---|---|---|
| Fluorinated aromatic compounds | | J. Am. Chem. Soc. 122, 1832 (2000) |
| Fullerene (e.g., C60) | | US20090101870 |
| Triazine complexes | | US20040036077 |
| Zn (N^N) complexes | | U.S. Pat. No. 6,528,187 |

EXPERIMENTAL

Chemical abbreviations used throughout this document are as follows: Cy is cyclohexyl, dba is dibenzylideneacetone, EtOAc is ethyl acetate, DME is dimethoxyethane, dppe is 1,2-bis(diphenylphosphino)ethane, dppf is 1,1'-Bis(diphenylphosphino)ferrocene, THF is tetrahydrofuran, DCM is dichloromethane, S-Phos is dicyclohexyl(2',6'-dimethoxy-[1,1'-biphenyl]-2-yl)phosphine.

Synthesis of Compound A

Preparation of 5-bromo-2-phenylpyridine

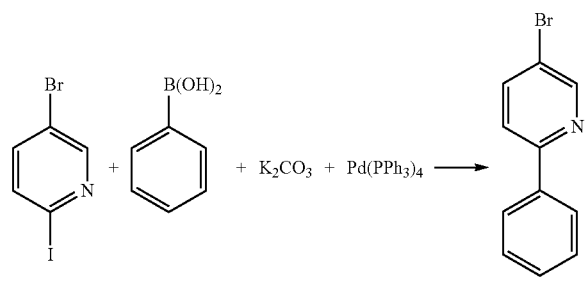

5-Bromo-2-iodopyridine (15 g, 52.8 mmol), phenylboronic acid (6.44 g, 52.8 mmol), Pd(Ph$_3$)$_4$ (0.611 g, 0.528 mmol) and potassium carbonate (83 g, 598 mmol) were added to a solution of 4:1 DME and water (260 mL). The reaction mixture was degassed with nitrogen gas for 30 minutes and was stirred at reflux for 18 hours in an inert environment. The reaction mixture was cooled, poured over water, and partitioned between brine and ethyl acetate. The organic layers were combined, dried over MgSO$_4$ and the organic solvent was removed under reduced pressure. The crude was purified by column chromatography over silica gel using 5-15% DCM/hexanes as eluent to produce (4.18 g, 33.8%) of 5-bromo-2-phenylpyridine as a white solid.

Preparation of 2-phenyl-5-(triisopropylsilyl)pyridine

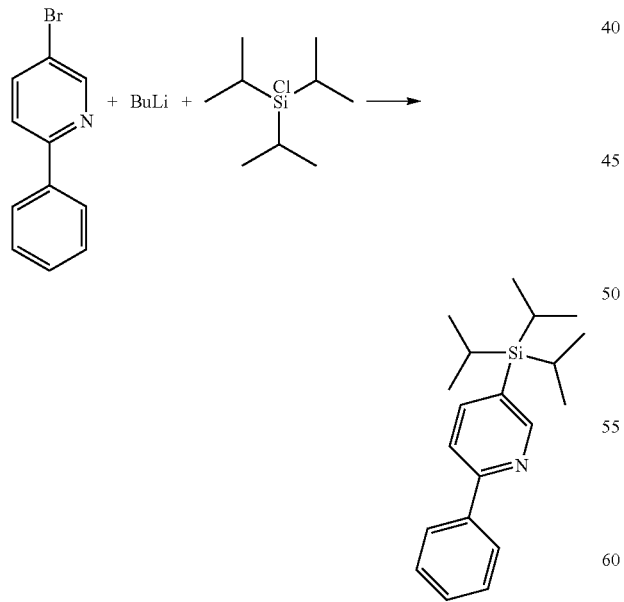

5-Bromo-2-phenylpyridine (3.21 g, 13.71 mmol) was dissolved in THF (200 mL). This was cooled to −78° C. To the cooled solution, 1.88 mL of 2.5M n-BuLi in hexanes was added drop wise. The reaction was monitored for the completion of lithium-halogen exchange by TLC. After complete lithiation, chlorotriisopropylsilane (2.185 mL, 16.46 mmol) dissolved in THF (15 mL) was slowly added to the reaction medium. The reaction temperature was kept at −78° C. for another 45 minutes before it was allowed to warm up to ambient temperature and stirred for another 48 h. The crude reaction mixture was quenched with saturated ammonium chloride solution and partitioned between brine and ethyl acetate. The aqueous layer was collected and rewashed with ethyl acetate. The organic layers were combined, dried over MgSO$_4$ and solvents were removed under reduced pressure. The light yellow color solid was purified by column chromatography over silica gel using 1-4% ethyl acetate in hexanes as eluent to afford (2.3 g, 54%) of 2-phenyl-5-(triisopropylsilyl)pyridine.

Preparation of Compound A

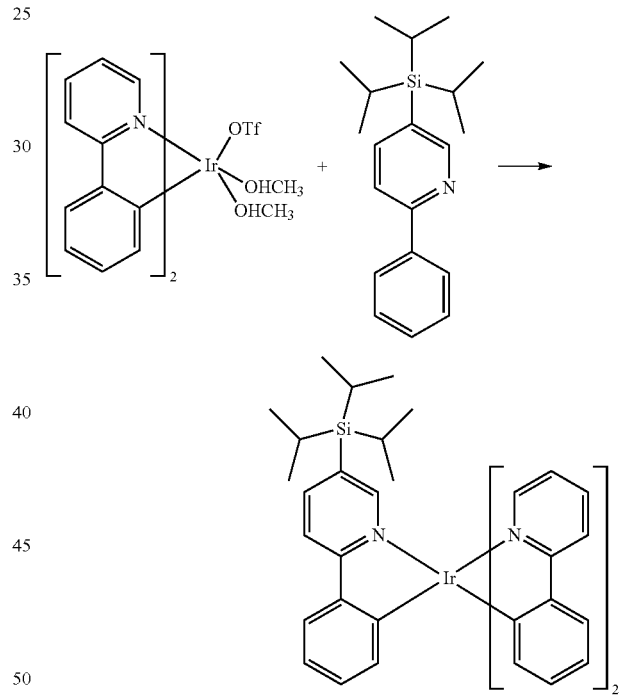

Iridium complex (1.77 g, 2.48 mmol) and 2-phenyl-5-(triisopropylsilyl)pyridine (2.32 g, 7.45 mmol) were added to ethanol (165 mL) and the slurry was degassed with bubbled nitrogen gas. The reaction mixture was heated to reflux for 24 hours. The reaction mixture was cooled down to ambient temperature, filtered through a bed of silica gel, such as Celite® diatomaceous earth distributed by Imersys Minerals California, Inc., and the precipitate was redissolved in dichloromethane. The crude material was purified by column chromatography using 2:1 (v/v) DCM/hexanes. The final compound was isolated after sublimation to give (1.03 g, 42%) of the desired product.

Synthesis of Compound B

Preparation of 4-bromo-2-phenylpyridine

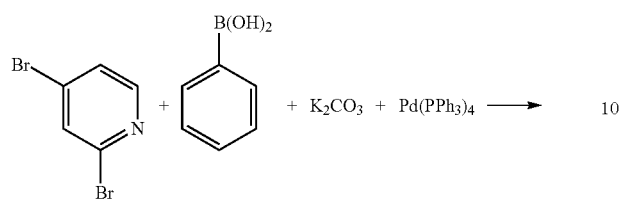

Into a 500 mL round-bottomed flask was placed 2,4-dibromopyridine (9.90 g, 41.8 mmol), phenylboronic acid (5.10 g, 41.8 mmol), and potassium carbonate (11.55 g, 84 mmol) in DME (100 mL). The reaction mixture was diluted with water (40 mL). This was degassed for 30 minutes and Pd(PPh$_3$)$_4$, (0.483 grams, 0.418 mmol) was added and the reaction was stirred at reflux for 22 hours. The mixture was diluted with brine and ethyl acetate. The organic layer was washed with water, dried and adsorbed onto Celite® and chromatographed on a 400 gram column eluted with 0-5% ethyl acetate in hexane giving the desired product (5.30 g, 54%) as clear colorless oil.

Preparation of 2-phenyl-4-(triisopropylsilyl)pyridine

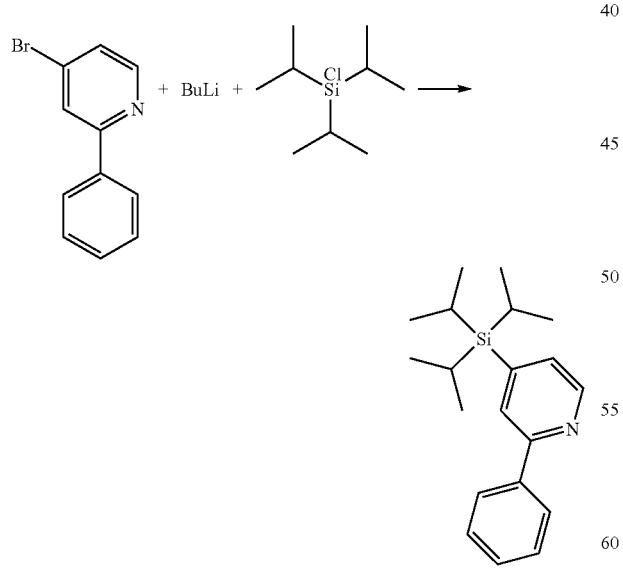

4-Bromo-2-phenylpyridine (4.25 g, 18.16 mmol) was dissolved in THF (200 mL) and cooled to −78° C. n-butyllithium (7.99 mL, 19.97 mmol) was added to the reaction mixture drop wise and this was stirred for another 30 minutes at −78° C. Chlorotriisopropylsilane (3.62 mL, 27.2 mmol) was slowly added to the reaction mixture and this was stirred and allowed to warm to room temperature. The crude reaction mixture was partitioned between brine and ethyl acetate. The organic layer was collected, dried over MgSO$_4$ and organic solvents were removed under reduced pressure. The crude product was purified by column chromatography using 1-5% ethyl acetate/hexanes as eluent over silica gel to afford (3.9 g, 69%) of the title compound.

Preparation of Compound B

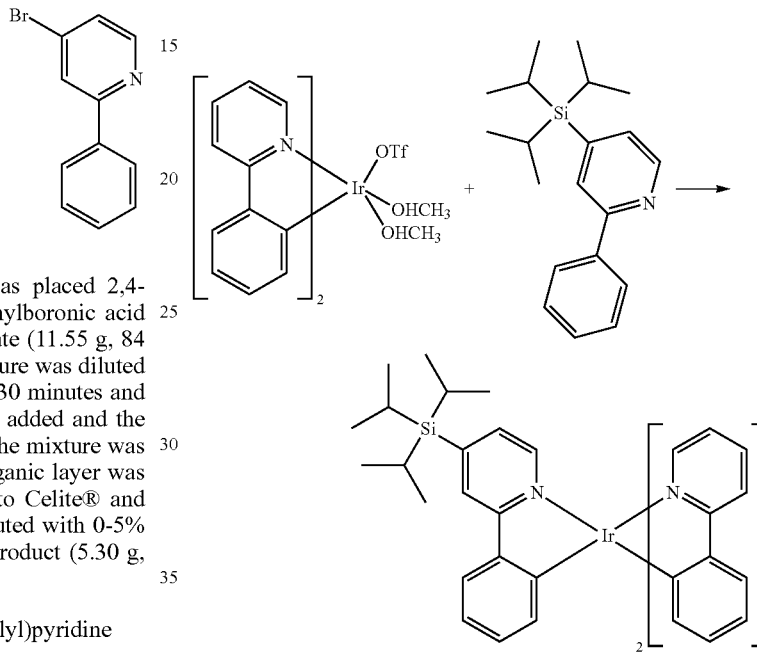

2-Phenyl-4-(tri-isopropylsilyl)pyridine (3.93 g, 12.61 mmol) and the iridium complex (3 g, 4.20 mmol) were added to ethanol (120 mL) and degassed with nitrogen gas. The reaction mixture was refluxed under nitrogen for 18 hours. The crude product was filtered through a Celite® plug and washed with ethanol. The leftover yellow residue was dissolved in DCM. Organic solvent was removed under vacuum. The yellow residue was purified by column chromatography using 2:1 (v/v) dichloromethane/hexanes as eluent over silica gel to obtain Compound B (1.7 g, 50%) as a yellow solid.

Synthesis of Compound C

Synthesis of 2-(3-bromophenyl)pyridine

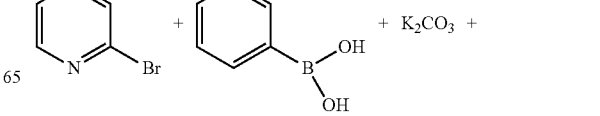

-continued

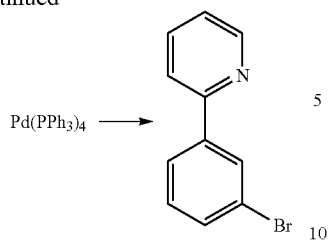

2-Bromopyridine (12.05 mLl, 127 mmol), 3-bromophenyl boronic acid (25.4 g, 127 mmol) and potassium carbonate (52.5 g, 380 mmol) were added to 9:1 mixture of toluene and water (600 mL). The reaction mixture was degassed with nitrogen gas for 15 minutes and Pd(PPh$_3$)$_4$ (1.463 g, 1.266 mmol) was added. The reaction mixture was degassed for another 30 minutes before heating to reflux under nitrogen gas for 18 hours. The crude reaction mixture was cooled to room temperature, filtered through a Celite® pad and the filtrate was partitioned between brine and ethyl acetate. The organic layers were combined, dried over MgSO$_4$ and the organic solvent was removed under reduced pressure. The crude product was purified by column chromatography over silica gel using 1-4% ethyl acetate/hexanes. 2-(3-bromophenyl) pyridine (10 g, 33.7%) was isolated as colorless oil.

Synthesis of 2-(3-(tri-isopropylsilyl)phenyl)pyridine

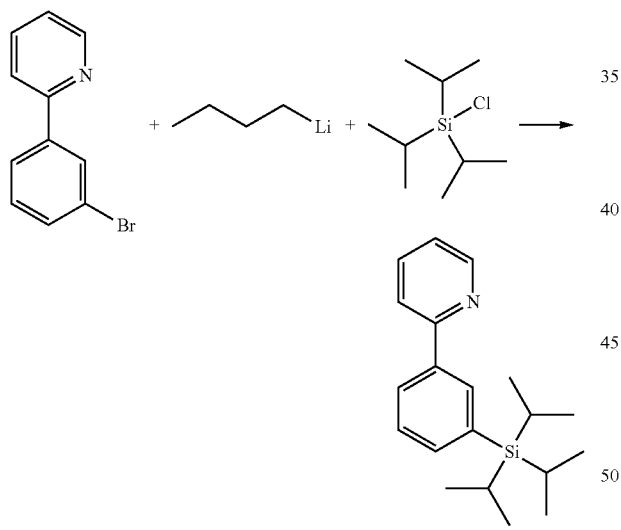

2-(3-Bromophenyl)pyridine (7.46 g, 31.9 mmol) was dissolved in THF (300 mL) in a 500 mL 3-neck round bottom flask. The system was evacuated and filled with nitrogen three times then maintained under nitrogen. The flask was placed in a dry ice/acetone bath and cooled to below −60° C. 2.5 M n-butyllithium (14.0 mL, 35.1 mmol) was added. The solution went from pale yellow to a dark green solution. After one hour, chlorotriisopropylsilane (10.91 mL, 51.0 mmol) was added via syringe in portions while keeping the reaction temperature below −60° C. before removal of the ice bath. The reaction was allowed to warm up to ambient temperature. After three hours, the reaction mixture was quenched with water then partitioned between brine and ethyl acetate. The aqueous portion was extracted with ethyl acetate two times. The combined organic layers were washed once with brine solution, dried over sodium sulfate, filtered and evaporated to produce an orange oil. The crude product was adsorbed onto Celite® and purified with chromatography using a mobile phase of 1-5% ethyl acetate in hexane to give (4.3 g, 43.3%) of the title compound as yellow oil.

Preparation of Compound C

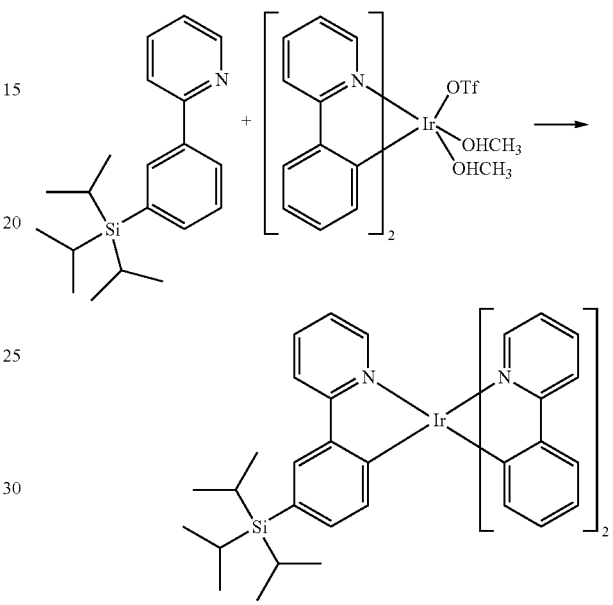

2-(3-(Triisopropylsilyl)phenyl)pyridine (7.19 g, 23.08 mmol), the iridium complex (5.49 g, 7.69 mmol) and ethanol (150 mL) were combined in a 250 mL single neck round bottom flask. The suspension was heated to a vigorous reflux overnight. The reaction was cooled to room temperature then filtered off to produce a bright yellow solid using a Celite® pad in a sintered filter funnel. The solid was washed well with ethanol. The crude product was recovered by washing the Celite® with DCM, then evaporating the filtrate down to a yellow solid. The solid was purified on a silica gel column eluted with 1:1 (v/v) hexane:dichloromethane. The desired fractions were combined and evaporated to afford (3.35 g, 53.7%) of Compound C as a yellow solid.

Synthesis of Compound D

Synthesis of 2-(4-bromophenyl)pyridine

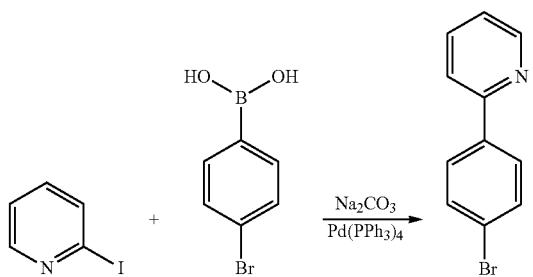

(4-Bromophenyl)boronic acid (10.17 g, 50.6 mmol) was added to a 500 mL 2-neck flask. The reaction mixture was diluted with DME (125 mL). 2-Iodopyridine (5.38 mL, 50.6 mmol) and sodium carbonate (10.73 g, 101 mmol) were added followed by water (50 mL). This mixture was degassed for 15 minutes with nitrogen and Pd(PPh$_3$)$_4$ (0.59 g, 0.506 mmol) was added. The reaction was stirred at reflux for 18 hours and cooled. DME (50 mL) and water (40 mL) were added to the reaction mixture. The resulting mixture was degassed again with nitrogen and additional Pd(PPh$_3$)$_4$ (0.59 g, 0.506 mmol) and 2.5 grams of additional boronic acid were added. This was reheated and stirred at reflux overnight. The crude product was diluted with ethyl acetate and water. The organic layer was concentrated and chromatographed on a 400 gram column eluted with 2-5% ethyl acetate in hexane to give (7.9 g, 67%) of desired product as white solid.

Synthesis of 2-(4-(triisopropylsilyl)phenyl)pyridine

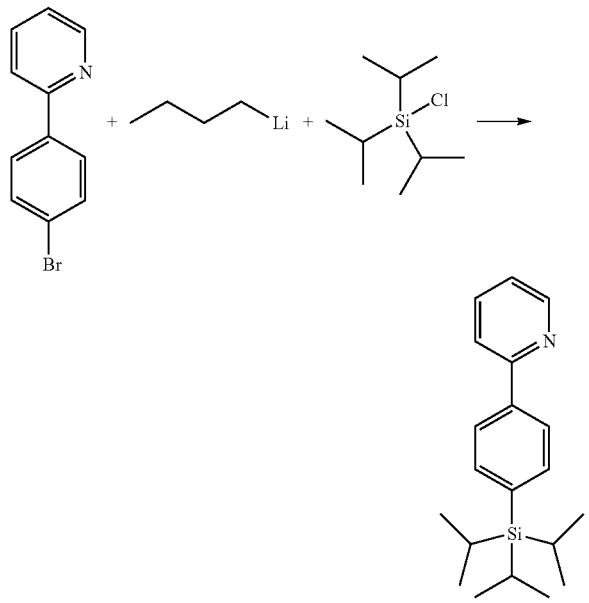

2-(4-Bromophenyl)pyridine (4.78 g, 20.42 mmol) was placed into a 500 mL 3-necked flask and dissolved in THF (200 mL) under a nitrogen atmosphere. The flask was placed in a dry ice/acetone bath and cooled to below −60° C. 2.5 M n-butyllithium (9.39 mL, 23.48 mmol) was added in portions via syringe through a septum while keeping the reaction temperature below −60° C. After 30 minutes, chlorotriisopropylsilane (5.24 mL, 24.50 mmol) was added rapidly via syringe in portions keeping the reaction temperature below −60° C. The reaction was allowed to warm up to room temperature over 3 hours. The reaction mixture was quenched with water then transferred to a separatory funnel with brine and ethyl acetate. The aqueous portion was extracted with ethyl acetate two times. The combined organic layers were washed once with saturated brine solution. The organic layer was dried with sodium sulfate, filtered and evaporated to give 8.5 g of the crude product as an orange oil. The crude product was adsorbed onto Celite® and purified with on silica together using 2-5% ethyl acetate in hexane. Vacuum distillation on a Kugelrohr gave the title compound as a yellow solid (2.42 g, 38%).

Preparation of Compound D

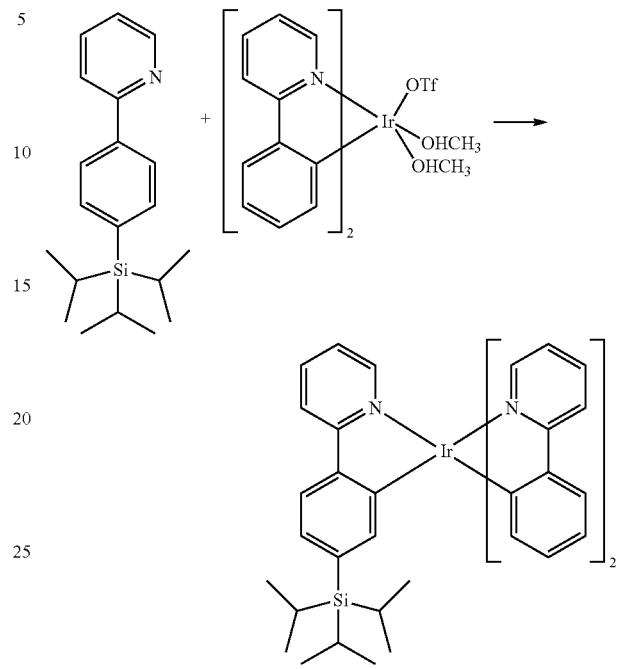

The iridium complex (2.29 g, 3.21 mmol), 2-(4-(triisopropylsilyl)phenyl)pyridine (3.0 g, 9.63 mmol) and ethanol (70 mL) were mixed in a 250 mL single neck round bottom flask. The suspension was heated to a vigorous reflux under nitrogen for 24 hours. The reaction was cooled to room temperature then filtered using a Celite® pad in a sintered filter funnel. The solid was washed well with ethanol. The filter cake was then washed with dichloromethane into another flask and the filtrate was evaporated to a bright yellow solid (1.46 g). The crude product was adsorbed onto Celite® and purified on silica gel using 75/25 then 50/50 hexane/dichloromethane (v/v) solvent system to obtain a bright yellow solid, (0.88 g, 47.4%).

Synthesis of Compound 1

Preparation of 2-phenyl-5-(triphenylsilyl)pyridine

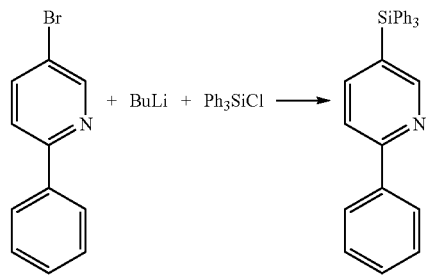

5-Bromo-2-phenylpyridine (3.0 g, 12.8 mmol) was dissolved in THF (200 mL). This solution was then cooled to −78° C. To the cooled solution, 1.88 mL 2.5M n-BuLi solution in hexanes was added drop wise. After complete lithium-halogen exchange, chlorotriphenylsilane (4.53 g, 15.38 mmol) dissolved in THF (15 mL) was slowly added to the reaction medium. The reaction temperature was kept at −78° C. for another 45 minutes before it was allowed to warm up to ambient temperature. After 2 hours the crude reaction mixture was quenched with saturated ammonium chloride solution and partitioned between brine and ethyl acetate. The aqueous layer was collected and rewashed with ethyl acetate. The combined organic layers were dried over MgSO₄ and solvents were removed under reduced pressure. The crude product was purified by column chromatography over silica gel using 1-4% ethyl acetate in hexanes as eluent to obtain 2-phenyl-5-(triphenylsilyl)pyridine (3.17 g, 60%) as a white solid.

Preparation of Compound 1

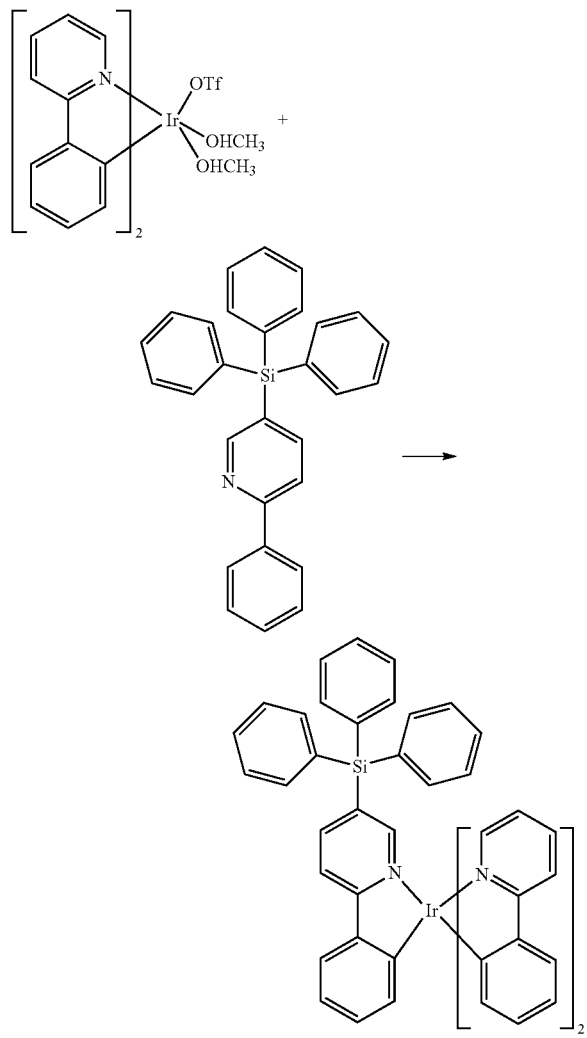

The iridium complex (2.186 g, 3.06 mmol) and 2-phenyl-5-(triphenylsilyl)pyridine (3.8 g, 9.19 mmol) were mixed in ethanol (56 mL) and heated to reflux under nitrogen for 18 hours. The reaction mixture was cooled to room temperature and filtered through a Celite® pad. The solid residue was collected and coated on Celite® and run through a silica gel plug using DCM as solvent to give 1.87 g of crude product. This product was chromatographed over silica gel using a 2:1 mixture (v/v) of hexanes:dichloromethane and further sublimed to obtain Compound 1 (0.85 g, 30.3%).

Synthesis of Compound 2

Synthesis of 2-phenyl-4-(triphenylsilyl)pyridine

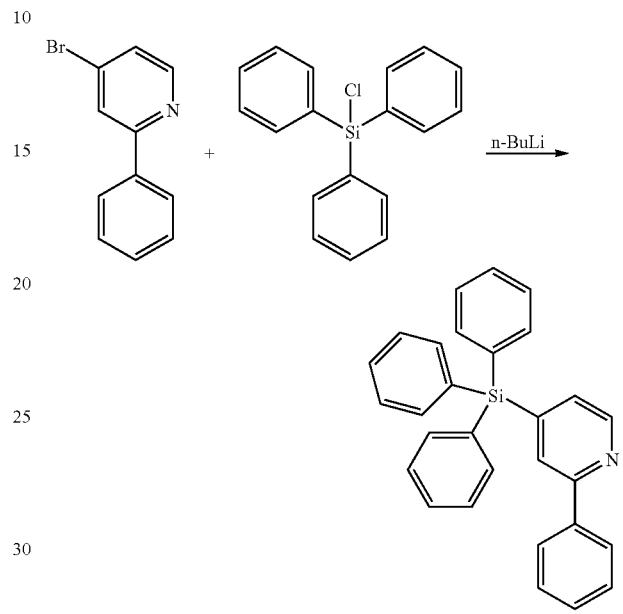

A 500 mL 2-neck flask was charged with 4-bromo-2-phenylpyridine (5.12 g, 21.87 mmol). The atmosphere in the flask was evacuated and backfilled with nitrogen. The reaction mixture was diluted with THF (200 mL) and this was placed in a dry-ice acetone bath. Next, n-butyllithium (9.62 mL, 24.06 mmol) was added and the reaction was stirred for 30 minutes before addition of chlorotriphenylsilane (7.74 g, 26.2 mmol) dissolved in THF (20 mL), and the bath was removed. After 2 hours the reaction was quenched with water and diluted with ethyl acetate and water. The organic layer was washed with brine then water and dried. The product was chromatographed on a 400 gram column eluted with 5-10% ethyl acetate in hexane to obtain the product as a white solid (6.64 g, 73%).

Preparation of Compound 2

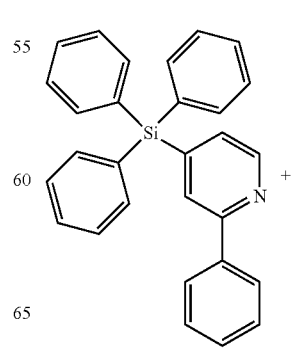

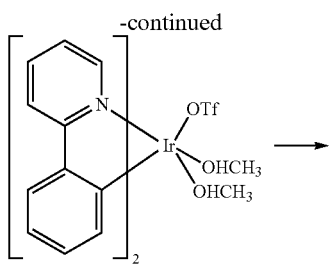

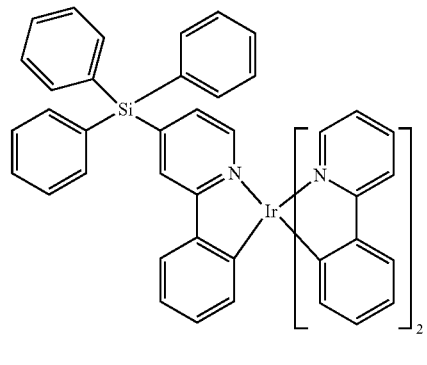

Into a 500 mL round-bottomed flask was placed 2-phenyl-4-(triphenylsilyl)pyridine (6.40 g, 15.47 mmol) and the iridium complex (3.68 g, 5.16 mmol) in ethanol (100 mL). This was stirred at reflux for 20 hours. The reaction mixture was filtered and washed with hexane and ethanol. Then the filtration funnel was placed on a different filtration flask and the crude product and Celite® were washed with DCM. The filtrate was evaporated to obtain 3.65 g of crude product. The crude product was chromatographed on 3×150 g silica gel columns eluting with 1:1 (v/v) DCM-hexane to afford 2.64 g of product. The product was suspended in acetonitrile (200 mL) and stirred at reflux for 13 hours. The mixture product was then cooled and filtered to obtain 2.2 grams. This was sublimed at 315° C. to give 1.68 g of Compound 2.

Synthesis of Compound 3

Preparation of 2-(3-(triphenylsilyl)phenyl)pyridine

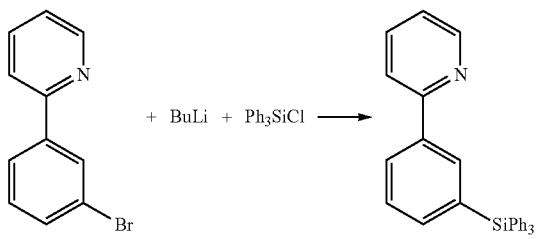

2-(3-bromophenyl)pyridine (5 g, 21.36 mmol) was dissolved in THF (214 mL) and cooled to −78° C. n-Butyl lithium (2.5M solution in hexanes, 9.40 mL, 23.50 mmol) was slowly added to the cooled reaction mixture and this was stirred for another 30 minutes in cold bath after complete addition. Chlorotriphenylsilane (7.56 g, 25.6 mmol) dissolved in THF (30 mL) was slowly added to the reaction mixture which was then allowed to come to room temperature and stirred for another 18 h. The reaction mixture was quenched with saturated $NH_4Cl$ solution. The reaction mixture was partitioned between brine and ethyl acetate. The organic layers were combined, dried over $MgSO_4$ and solvents were removed under reduced pressure. The off-white crude product was purified by column chromatography over silica gel using 2-8% ethyl acetate/hexanes as eluent. The isolated oily material was recrystallized from hexanes/DCM to obtain 2-(3-(triphenylsilyl)phenyl)pyridine (6.91 g, 78%) as a white crystalline solid.

Preparation of Compound 3

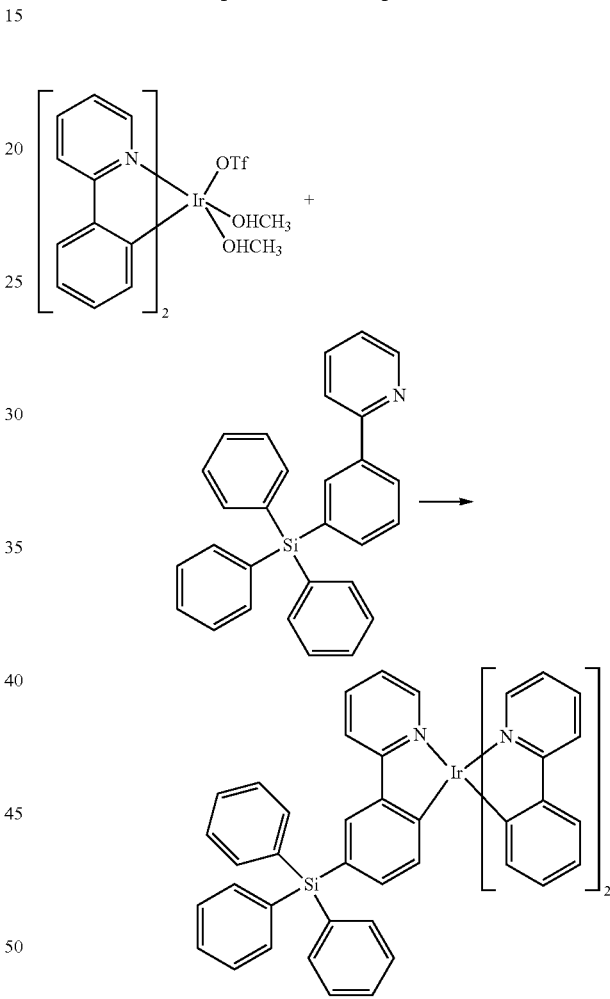

The iridium complex (3.74 g, 5.24 mmol) and 2-(3-(triphenylsilyl)phenyl)pyridine (6.5 g, 15.72 mmol) were added to ethanol (150 mL) and degassed by bubbling nitrogen gas for 30 minutes. The reaction mixture was refluxed under nitrogen for 18 h. The cooled reaction mixture was filtered through a Celite® pad. The collected solid was washed with ethanol followed by hexanes. The precipitate was dissolved in DCM. Organic solvents were removed under reduced pressure to yield a light yellow color solid which was further purified by column chromatography using 7:3 (v/v) DCM:hexanes. Compound 3 (2 g, 41.8%) was isolated as bright yellow solid after further purification by sublimation.

Synthesis of Compound 4

Synthesis of 2-(3-(methyldiphenylsilyl)phenyl)pyridine

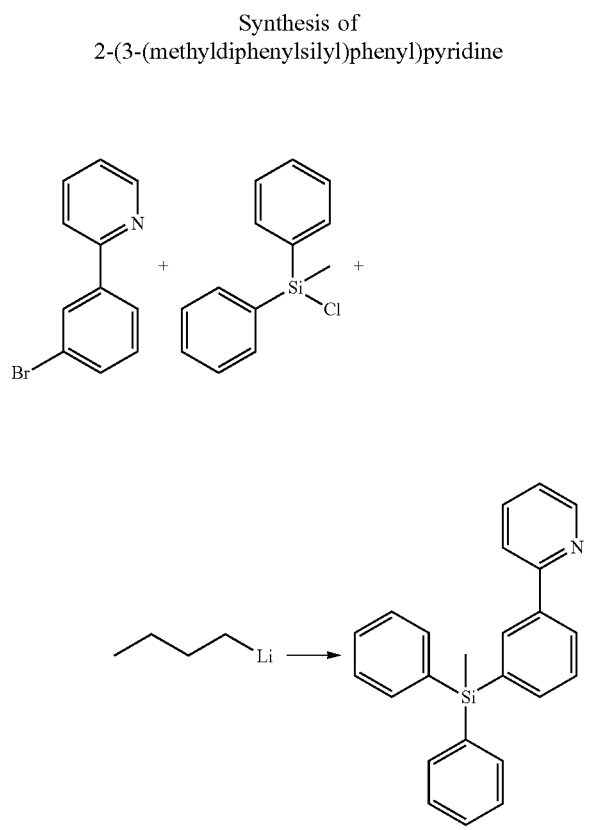

2-(3-Bromophenyl)pyridine (3 g, 12.82 mmol) was added to dry THF (250 mL) and was cooled to −78° C. Chloro(methyl)diphenylsilane (4.24 mL, 19.22 mmol) was added drop wise to the solution and allowed to stir to room temperature for 18 hours. The reaction mixture was quenched with saturated ammonium chloride solution. The crude product was partitioned between brine and ethyl acetate. Organic layers were combined, dried and solvents were removed under reduced pressure. The isolated product was purified by silica gel column chromatography using 1-5% ethyl acetate/hexanes as eluent. The isolated material was further purified by distillation to give 2-(3-(methyldiphenylsilyl)phenyl)pyridine (3.9 g, 69%).

Preparation of Compound 4

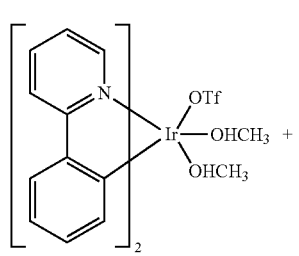

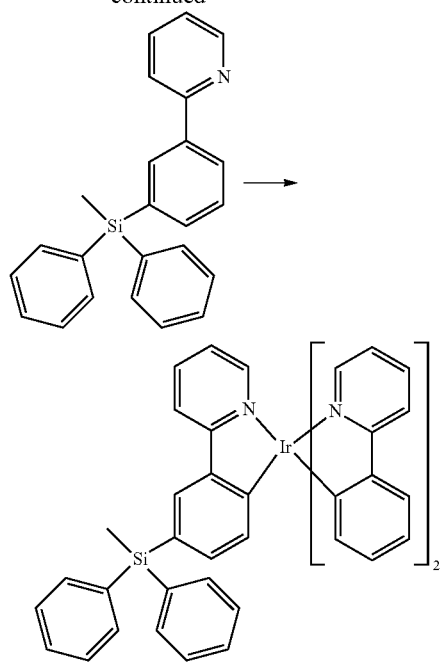

The iridium complex (2.234 g, 3.13 mmol) and 2-(3-(methyldiphenylsilyl)phenyl)pyridine (33 g, 9.39 mmol) were added to 1:1 mixture of ethanol and methanol and degassed by bubbling nitrogen gas for 30 minutes. The reaction mixture was heated to reflux for 18 hours after which time the reaction mixture was cooled and filtered through a Celite® pad. The residue was washed with ethanol followed by hexanes and then dissolved in dichloromethane. Organic solvents were removed under reduced pressure and the crude product was purified by silica gel column chromatography using 7:3 (v/v) DCM:hexanes as eluent to obtain (0.97 g, 51%) of desired product was isolated after sublimation.

Synthesis of Compound 5

Synthesis of 2-(4-(triphenylsilyl)phenyl)pyridine

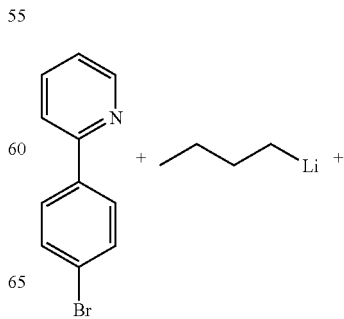

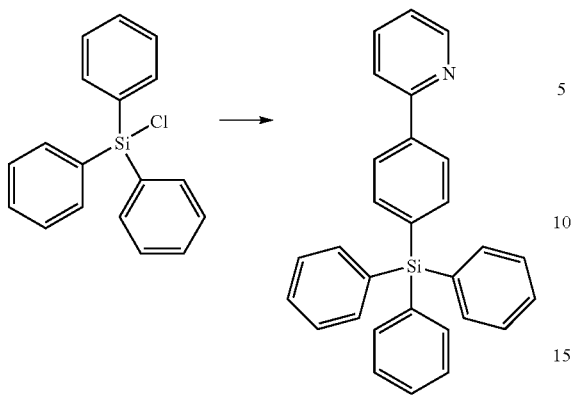

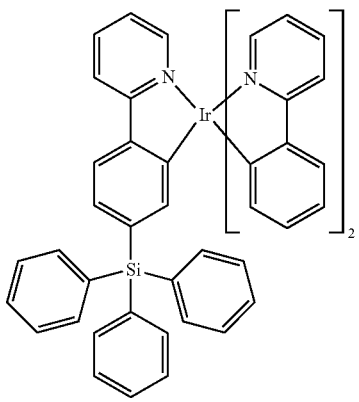

2-(4-Bromophenyl)pyridine (3.0 g, 12.82 mmol) was added to a 250 mL 3-necked flask. This was evacuated and backfilled with nitrogen. The reaction mixture was diluted with TI-IF (120 mL) and the flask was placed in a dry-ice acetone bath. n-butyllithium (5.64 mL, 14.10 mmol) was added and the solution went from pale yellow to green and a precipitate formed. Chlorotriphenylsilane (4.53 grams, 15.4 mmol) was placed in a separate flask under nitrogen and dissolved in THF (15 mL). After 30 minutes the chlorotriphenylsilane was added and the dry-ice bath was removed. The reaction was stirred to ambient temperature and became a pale yellow clear solution. After 2 hours the reaction mixture was diluted with brine and ethyl acetate. The organic layer was washed with water, dried and adsorbed onto Celite®. Chromatography on a 200 gram column eluted with 5-10% ethyl acetate in hexane to provide the desired product as a white solid (4.1 g, 77%).

Preparation of Compound 5

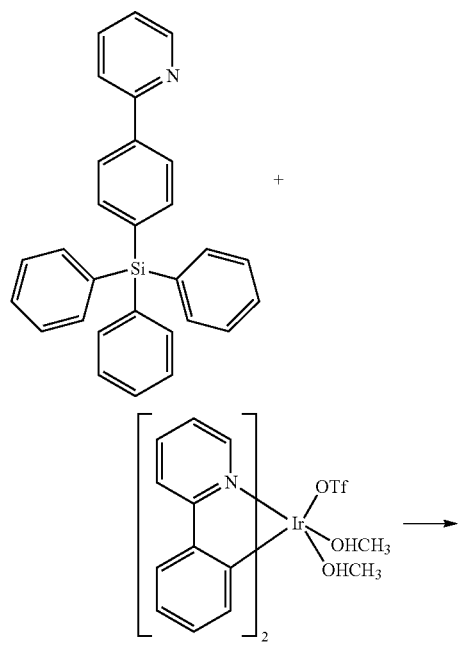

The iridium complex (2.301 g, 3.22 mmol) and 2-(4-(triphenylsilyl)phenyl)pyridine (4.0 g, 9.67 mmol) were added to a 250 mL 3-necked flask. The reaction mixture was diluted with ethanol (100 mL) and the reaction was stirred at reflux for 20 hours. This reaction mixture was then filtered through Celite®, washing with hexane then ethanol. The filter funnel was then placed on a different flask and the filter cake was washed with dichloromethane. The filtrate was evaporated to a crude yellow solid which was chromatographed on silica gel using a mobile phase of 1:1 (v/v) DCM:hexane to get 1.8 g of product, which was sublimed to obtain pure Compound 5 (1.32 g, 63%).

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound selected from the group consisting of:

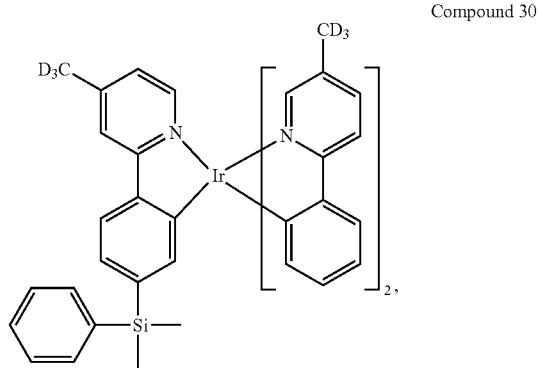

Compound 30

-continued

Compound 31
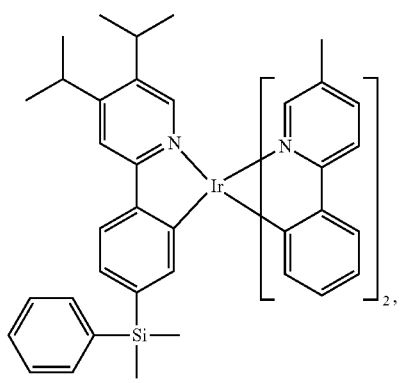

Compound 32
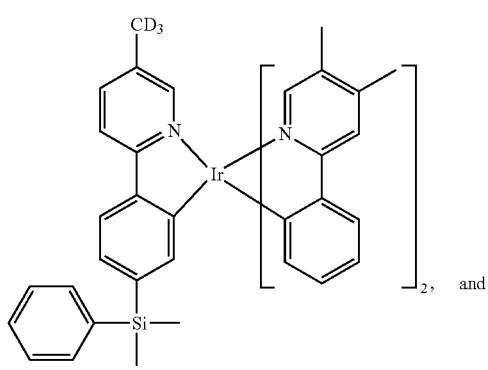, and

Compound 33
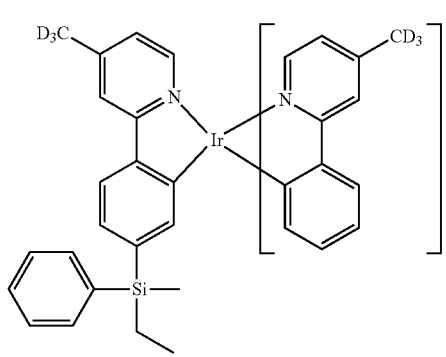

2. The compound of claim 1, wherein the compound is

Compound 30
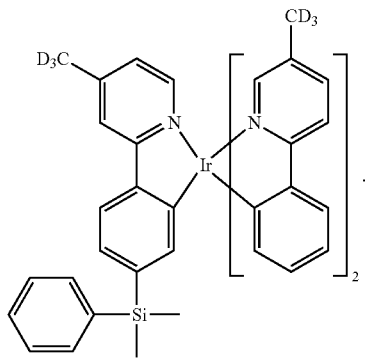

3. The compound of claim 1, wherein the compound is

Compound 31
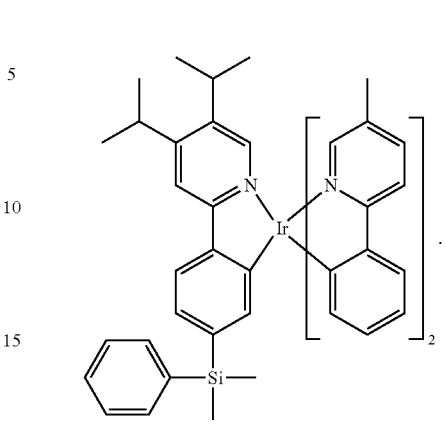

4. The compound of claim 1, wherein the compound is

Compound 32
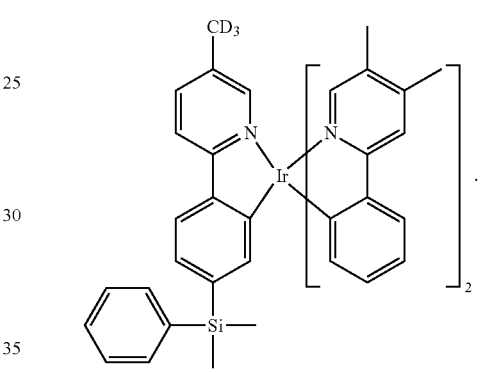

5. The compound of claim 1, wherein the compound is

Compound 33
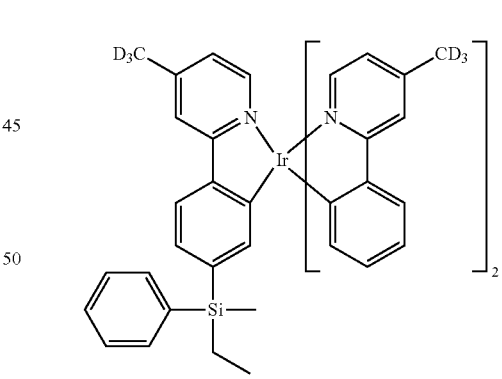

6. A first device comprising a first organic light emitting device, the first organic light emitting device comprising:
   an anode;
   a cathode; and
   an organic layer, disposed between the anode and the cathode, comprising a compound of claim 1.

7. The first device of claim 6, wherein the first device is selected from the group consisting of a consumer product, an organic light-emitting device, and a lighting panel.

8. The first device of claim 6, wherein the organic layer is an emissive layer and the compound is an emissive dopant.

9. The first device of claim 6, wherein the organic layer is an emissive layer and the compound is a non-emissive dopant.

10. The first device of claim 6, wherein the organic layer further comprises a host.

11. The first device of claim 10, wherein the host comprises a triphenylene containing benzo-fused thiophene or benzo-fused furan;

wherein any substituent in the host is an unfused substituent independently selected from the group consisting of $C_nH_{2n+1}$, $OC_nH_{2n+1}$, $OAr_1$, $N(C_nH^{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$ and $C_nH_{2n}-Ar_1$;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

12. The first device of claim 10, wherein the host is selected from the group consisting of:

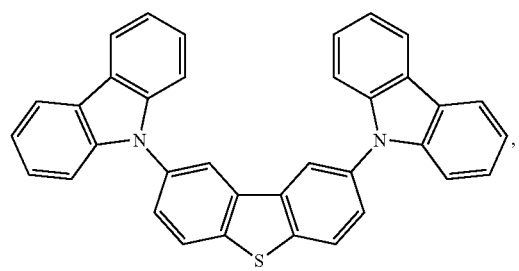,

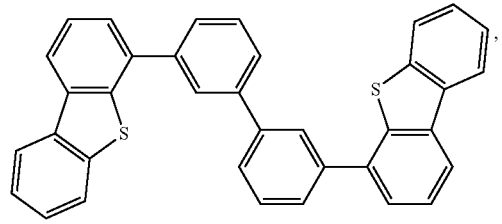,

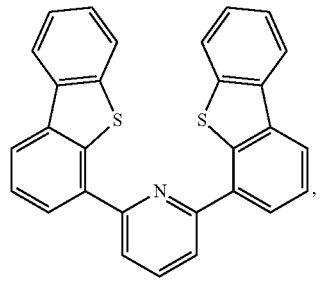,

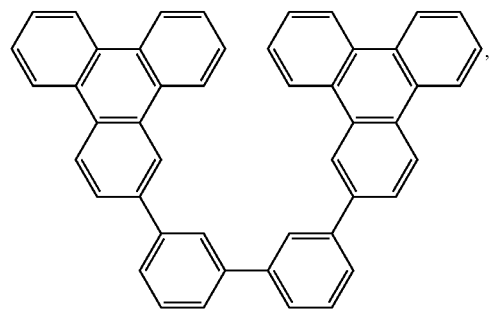,

-continued

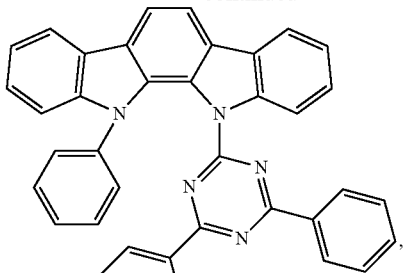,

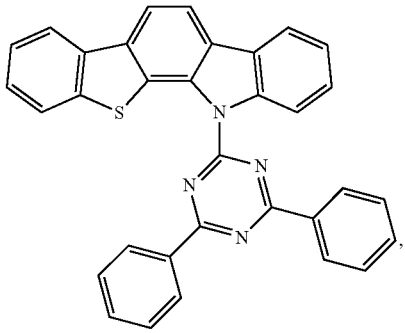,

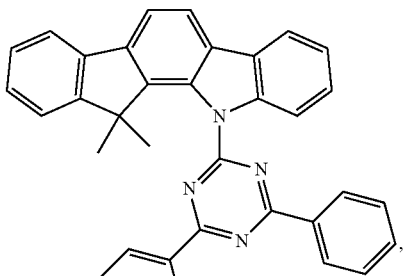,

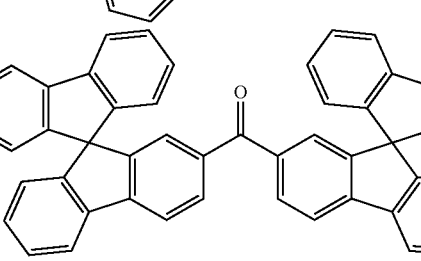,

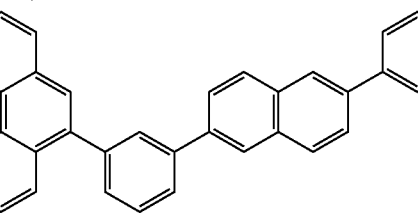,

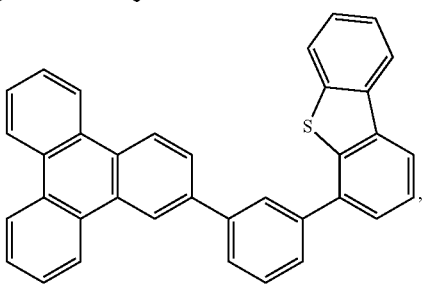,

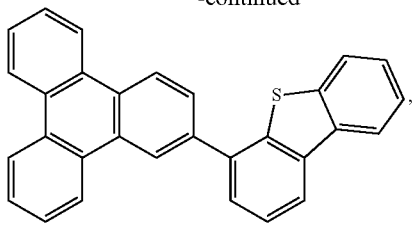
and combinations thereof.
13. The first device of claim 10, wherein the host comprises a metal complex.
* * * * *